(12) United States Patent
Stabelfeldt et al.

(10) Patent No.: US 9,867,743 B2
(45) Date of Patent: Jan. 16, 2018

(54) ABSORBENT ARTICLE HAVING A PRIMARY FASTENING SYSTEM AND A SECONDARY FASTENING SYSTEM

(71) Applicant: KIMBERLY-CLARK WORLDWIDE, INC., Neenah, WI (US)

(72) Inventors: Sara Jane Wille Stabelfeldt, Appleton, WI (US); David Fleger Bishop, Appleton, WI (US); Wendy Lynn VanDyke, Appleton, WI (US); Robert Lee Popp, Greenville, WI (US); David John Enz, Neenah, WI (US); Catherine Marguerite Hancock-Cooke, Neenah, WI (US); Alanna Haessler, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 15/121,113

(22) PCT Filed: Apr. 30, 2014

(86) PCT No.: PCT/US2014/036179
§ 371 (c)(1),
(2) Date: Aug. 24, 2016

(87) PCT Pub. No.: WO2015/167533
PCT Pub. Date: Nov. 5, 2015

(65) Prior Publication Data
US 2017/0065468 A1    Mar. 9, 2017

(51) Int. Cl.
*A61F 13/15*    (2006.01)
*A61F 13/56*    (2006.01)
(Continued)

(52) U.S. Cl.
CPC .... *A61F 13/5633* (2013.01); *A61F 13/49004* (2013.01); *A61F 13/49017* (2013.01);
(Continued)

(58) Field of Classification Search
CPC .... A61F 13/622; A61F 13/62; A61F 13/5638; A61F 13/5633; A61F 13/5644; A61F 13/49007
(Continued)

(56) References Cited

U.S. PATENT DOCUMENTS 5,772,649 A * 6/1998 Siudzinski ............ A61F 13/493
604/386
6,524,293 B1 2/2003 Elsberg et al.
(Continued)

FOREIGN PATENT DOCUMENTS

CN    102149356 A    8/2011

OTHER PUBLICATIONS

International Search Report for International Application No. PCT/US2014/036179, dated Mar. 7, 2016, 15 pages.
(Continued)

*Primary Examiner* — Jacqueline Stephens
(74) *Attorney, Agent, or Firm* — Armstrong Teasdale LLP

(57) ABSTRACT

An absorbent article includes a chassis having longitudinally opposite ends, transversely opposite sides, a bodyside liner at least in part defining the inner surface of the article, an outer cover at least in part defining the outer surface of the article, and an absorbent core disposed between the liner and the outer cover. A pair of ears extends transversely outward from the opposite sides of the chassis at the second waist portion thereof. A primary fastening system has a primary first fastening component located on each of the pair of ears and a primary second fastening component. A secondary fastening system has a secondary second fastening compo-
(Continued)

nent located on each of the ears and corresponding secondary first fastening components. A non-linear strip attached to an outer surface of the article includes the primary second fastening component and the secondary first fastening components.

17 Claims, 17 Drawing Sheets

(51) Int. Cl.
  *A61F 13/62* (2006.01)
  *A61F 13/49* (2006.01)
(52) U.S. Cl.
  CPC ........ *A61F 13/5644* (2013.01); *A61F 13/622* (2013.01); *A61F 13/49007* (2013.01); *A61F 13/5638* (2013.01); *A61F 13/62* (2013.01)
(58) Field of Classification Search
  USPC .................... 604/391, 385.01, 387, 394, 396
  See application file for complete search history.

(56) References Cited

U.S. PATENT DOCUMENTS

| | | |
|---|---|---|
| 2003/0100880 A1 | 5/2003 | Magee et al. |
| 2004/0111076 A1 | 6/2004 | Sayama et al. |
| 2008/0077101 A1 | 3/2008 | Waksmundzki et al. |
| 2008/0183147 A1 | 7/2008 | Kline et al. |

OTHER PUBLICATIONS

International Preliminary Report on Patentability for Application No. PCT/US2014/036179, dated Jul. 25, 2016.

* cited by examiner

ABSORBENT ARTICLE HAVING A PRIMARY FASTENING SYSTEM AND A SECONDARY FASTENING SYSTEM

BACKGROUND

The present disclosure relates to generally to absorbent articles intended for personal wear, and more particularly to disposable absorbent articles having a primary fastening system and a secondary fastening system for selectively fastening and refastening the article about the wearer.

Many absorbent articles intended for personal wear, such as diapers, training pants, feminine hygiene products, adult incontinence products, bandages, medical garments and the like are designed to be sufficiently absorbent to absorb moisture from liquid body exudates including urine, menses, blood, etc., away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste.

For articles where the attachment is refastenable, such as diapers and some training pants, pop-opens (separation of the fasteners) can sometimes occur as a result of stresses placed on the attachment by movement of the wearer. For example, and particularly for absorbent articles employing only one fastening system, as an infant or other wearer of the absorbent article moves about (e.g., crawls, walks, runs, bends, etc.) the shear stress placed on the fastening system due to the infant's movement may cause fastening tabs or the like to loosen or even come unfastened completely, resulting in an absorbent article which tends to leak, sag, or fall off of a wearer.

Accordingly, some known absorbent articles comprise more than one fastening system and/or fasteners to reduce the likelihood of the article leaking, sagging, falling off the user, etc. For example, FIG. 1 illustrates a known diaper, indicated generally at 10, comprising two fastening systems: a primary fastening system and a secondary fastening system. FIG. 1 depicts the diaper 10 in an unfolded and laid flat condition to show an outer cover 32 of the diaper which faces away from a wearer when the diaper is worn. The diaper 10 has a longitudinal direction 12 and a lateral direction 14.

In the longitudinal direction 12, the diaper 10 defines a front portion 16, a back portion 18, and a crotch portion 20 extending between and connecting the front portion and the back portion. The diaper 10 also includes a bodyside liner 30 (facing away from the view depicted in FIG. 1), and an absorbent core 34 located between the bodyside liner and the outer cover 32. The diaper 10 has opposite longitudinal side edges 28 that extend between a back waist edge 38 and a front waist edge 40. The diaper 10 also includes a pair of longitudinally-extending leg cuffs 36. The leg cuffs 36 may be adapted to fit about the legs of a wearer in use and serve as a mechanical barrier to the lateral flow of body exudates.

The back portion 18 of the diaper 10 includes a pair of back ears, indicated generally at 22. Each ear 22 includes a primary first fastening component 24 as part of the primary fastening system used to secure the diaper 10 around the waist of a wearer. The primary fastening system also comprises a primary second fastening component 76 for selectively receiving and fastening to the primary first fastening components 24. For example, the diaper 10 can be selectively moved from an unfastened configuration (as seen in FIG. 1) to a fastened or wear configuration by attaching the back waist region 18 (and more specifically the back ears 22) to the front waist region 16 to define a three-dimensional wear configuration of the diaper having a waist opening 50 and a pair of leg openings 52 (FIGS. 2 and 3). More particularly, the diaper 10 can be selectively moved from the unfastened configuration to the wear configuration by fastening the primary first fastening components 24 to the primary second fastening components 76 as is well known in the art.

The diaper 10 also includes a secondary fastening system comprising secondary first fastening components 26 and secondary second fastening components 78. For example, the illustrated diaper 10 comprises a pair of secondary first fastening components 26 as part of the front portion 16 of the diaper, with a secondary second fastening component 78 provided on each back ear 22. In such configurations, when the diaper 10 is moved to the wear configuration, the secondary first fastening components 26 engages the back portion 18 of the diaper (and more particularly, the secondary second fastening components 78 provided on the back ears 22) such that both the primary fastening system and the secondary fastening system secure the diaper around the waist of a wearer.

However, providing the secondary first fastening components 26 on the diaper 10 may pose drawbacks when the diaper is ultimately worn. For example, a stiffness or similar properties of the secondary first fastening components 26 may lead to discomfort or decreased mobility for a wearer of the diaper 10. For example, when wearing the diaper 10, an infant may crawl, walk, run, bend, etc., in such a manner that the front portion 16 of the diaper moves, bends, or otherwise deforms. Thus, if the secondary fastening system (and more particularly the secondary first fastening components 26 disposed on the front portion 16 of the diaper 10) is too stiff, the user may have decreased mobility as the front portion of the diaper may not be as readily deformed as if the secondary fastening system was omitted from the diaper. Further, a relatively stiff secondary fastening system may be uncomfortable to a wearer with the relatively unpliable secondary first fastening components 26 providing irritation when the wearer moves.

Moreover, the positioning of the secondary first fastening components 26 may also lead to discomfort for a wearer of the diaper 10. As seen in FIG. 3, for example, the secondary first fastening components 26 can contact the skin of the wearer during use of the diaper 10 if they are not positioned properly on the front portion 16 of the diaper. Skin contact by the secondary first fastening components 26, which are often hook fasteners, can produce red-marking and other skin irritation. More specifically, when the diaper 10 is donned, as seen in FIGS. 2 and 3, the lateral sides of the front portion 16 of the diaper are often gathered or otherwise compressed adjacent the leg openings 52. When this occurs and as illustrated in FIG. 3, the secondary first fastening components 26 can come into direct contact with the skin of the wearer, which in the illustrated diaper 10 the wearer is an infant or a toddler. As the wearer moves his/her legs, the secondary first fastening components 26 will rub against the leg causing skin irritation or red marking.

There is a need, therefore, for an improved fastening system provided on an absorbent article which provides for increased protection against leakage and secure attachment of the absorbent article without the associated discomfort discussed above.

SUMMARY

In one aspect, an absorbent article has an inner surface, an outer surface, a first waist portion, a second waist portion, and a crotch portion extending longitudinally between and connecting the first waist portion and the second waist portion. The absorbent article generally comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. A pair of ears extends transversely outward from the opposite sides of the chassis at the second waist portion thereof. A fastening system comprises a primary fastening system and a secondary fastening system. The primary fastening system comprises a primary first fastening component located on each of the pair of ears and a primary second fastening component. The secondary fastening system comprises a secondary second fastening component located on each of the ears and corresponding secondary first fastening components. A non-linear strip is attached to the outer surface of the article at the first waist portion. The primary second fastening component and the secondary first fastening components are located on the non-linear strip.

In another aspect, an absorbent article has an inner surface, an outer surface, a first waist portion, a second waist portion, and a crotch portion extending longitudinally between and connecting the first waist portion and the second waist portion. The absorbent article generally comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. A pair of ears extends transversely outward from the opposite sides of the chassis at the second waist portion thereof. A fastening system comprises a primary fastening system and a secondary fastening system. The primary fastening system comprises a primary first fastening component located on each of the pair of ears and a primary second fastening component. The secondary fastening system comprises a secondary second fastening component located on each of the ears and corresponding secondary first fastening components. A strip is attached to the outer surface of the article at the first waist portion. The primary second fastening component and the secondary first fastening components are located on the strip. The strip has a pair of spaced cutouts with each of the cutouts including one of the secondary first fastening components.

In yet another aspect, an absorbent article has an inner surface, an outer surface, a first waist portion, a second waist portion, and a crotch portion extending longitudinally between and connecting the first waist portion and the second waist portion. The absorbent article generally comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. A pair of ears extends transversely outward from the opposite sides of the chassis at the second waist portion thereof. Each of the ears has a medial line. A fastening system comprises a primary fastening system and a secondary fastening system. The primary fastening system comprises a primary first fastening component located on each of the pair of ears and a primary second fastening component. The secondary fastening system comprises a secondary second fastening component located on each of the ears and corresponding secondary first fastening components. Each of the primary first fastening component is located below the medial line.

BRIEF DESCRIPTION OF THE DRAWINGS

Corresponding reference characters indicate corresponding parts throughout the several views of the drawings.

DETAILED DESCRIPTION OF THE DRAWINGS

According to some aspects of the disclosure, an absorbent article is provided which overcomes at least some of the deficiencies of the conventional diapers described above. More particularly, according to some aspects of the disclosure, the absorbent article includes a secondary fastening system in order to securely attach the absorbent article around the waist of a wearer, but which comprises improved pliability and/or positioning over known fastening systems such that the absorbent article remains securely fastened even as the wearer crawls, walks, runs, bends, etc. without causing skill irritation or red marking. Thus, the secondary fastening system of the present disclosure may be constructed of suitable materials and disposed in a suitable position relative to other components of the absorbent article such that the absorbent article may be used without the drawbacks of the known diapers discussed above.

Figure 1:
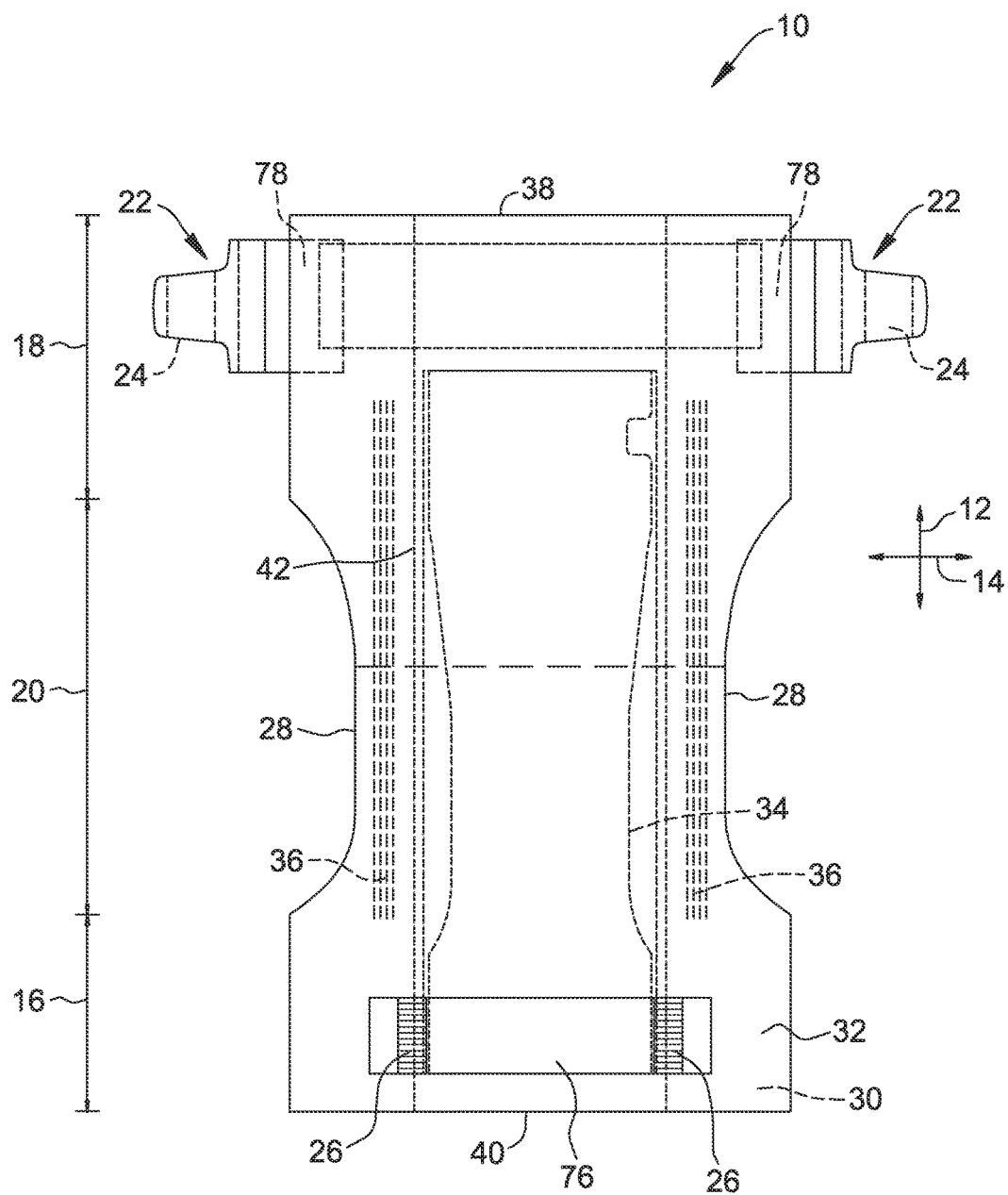
FIG. 1 is a top plan view of a prior art diaper in an unfolded and laid flat condition to show an outer surface of the diaper which faces away from the wearer when the diaper is worn.
Figure 2:
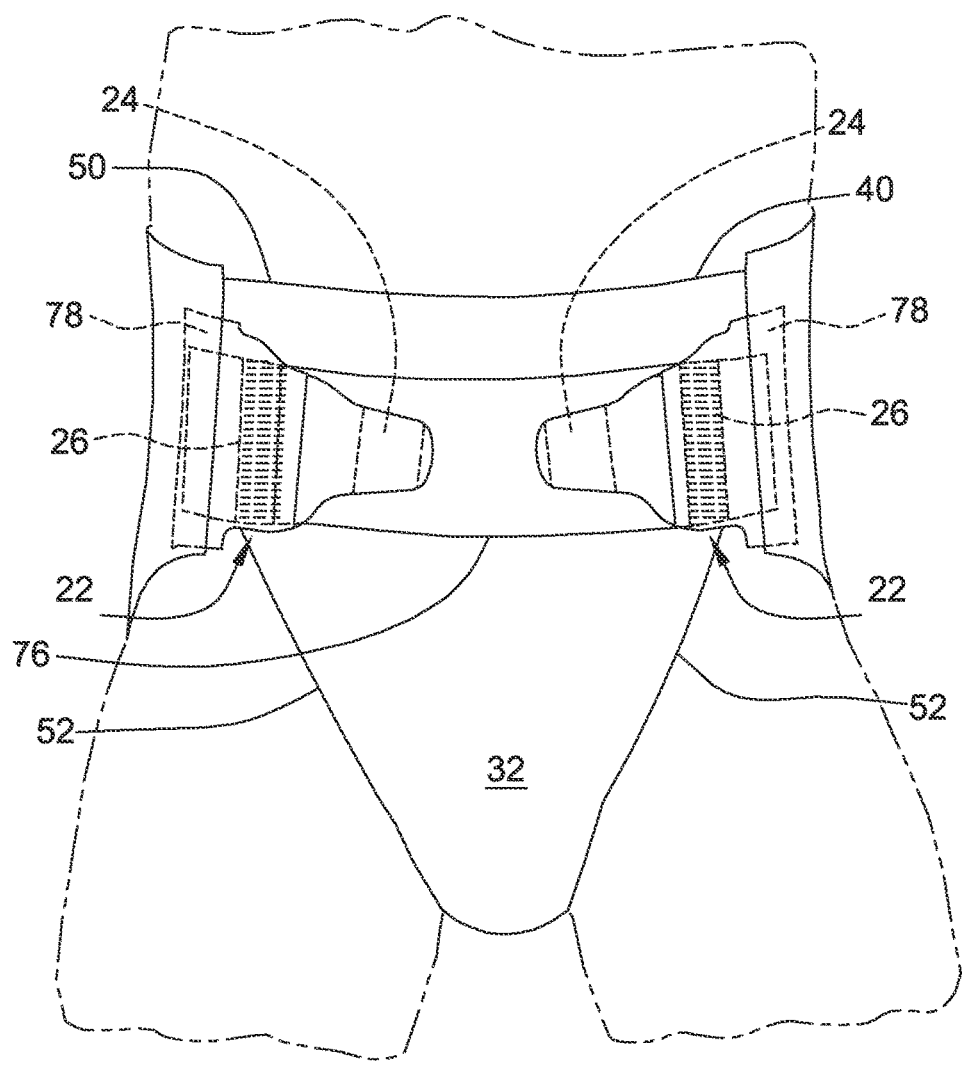
FIG. 2 is a perspective view of the prior art diaper of FIG. 1 in a wearer configuration and donned by a wearer.
Figure 3:
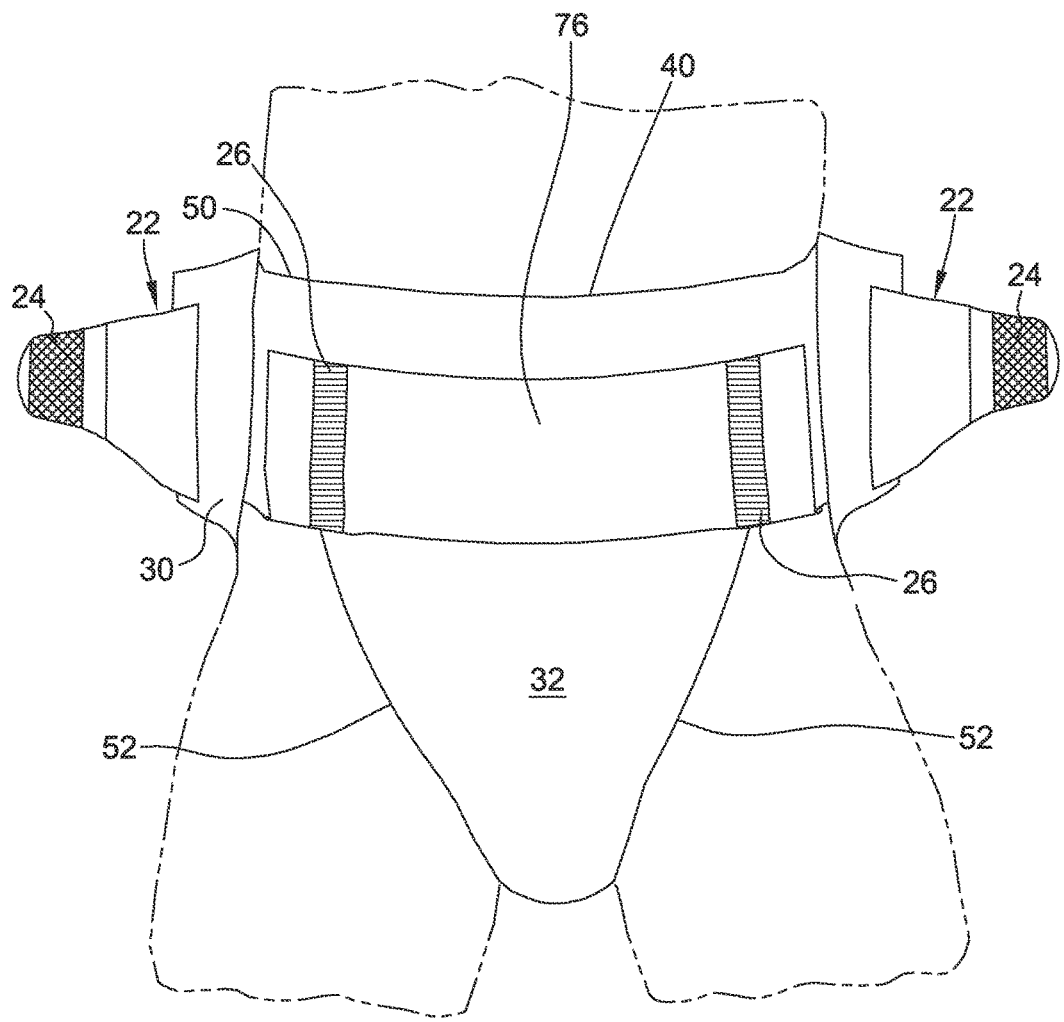
FIG. 3 is a perspective view of the prior art diaper seen in FIG. 2 with a fastening system unfastened to illustrate secondary first fastening components of the fastening system contacting the skin of the wearer.
Figure 4:
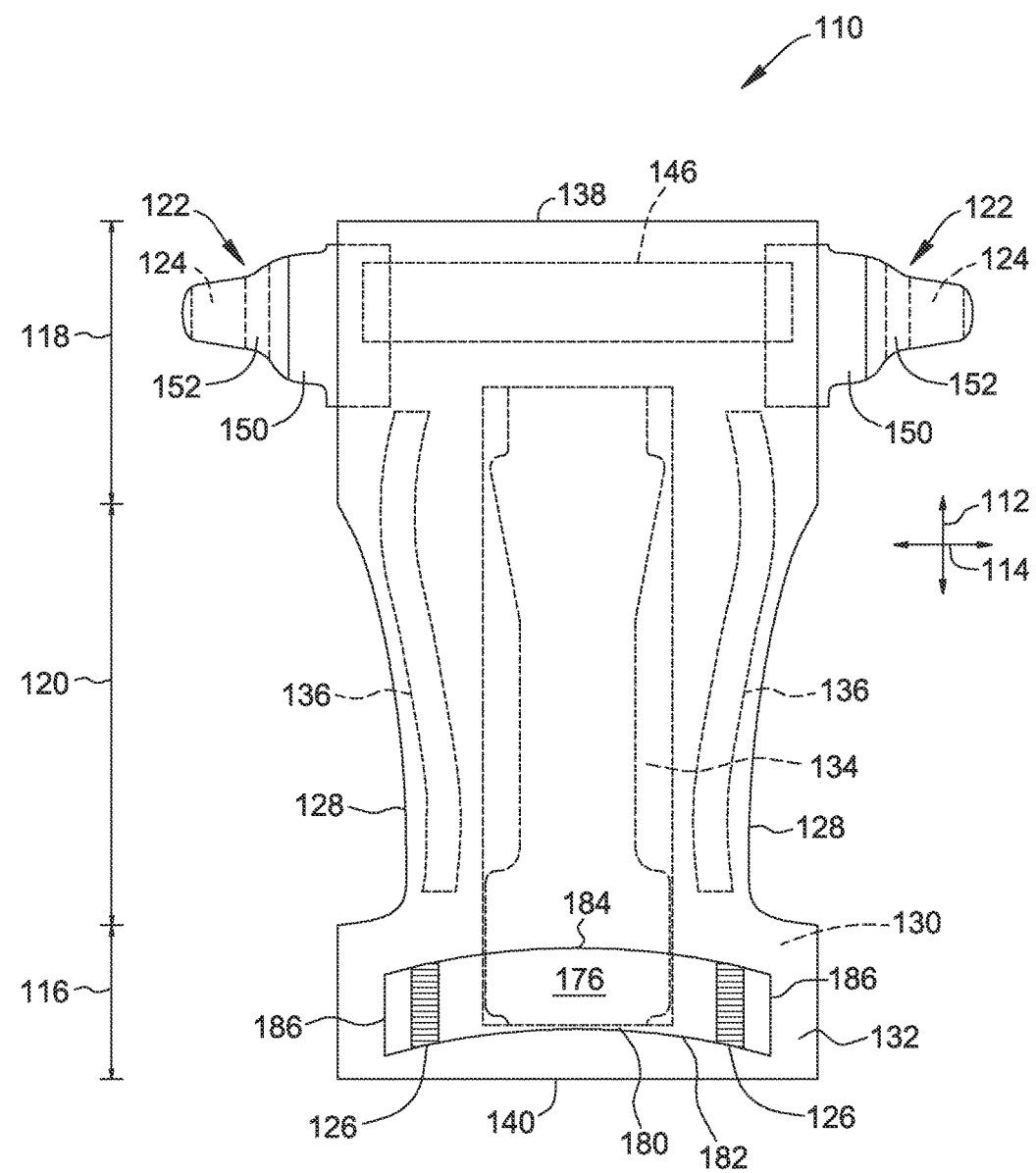
FIG. 4 is a top plan view of a diaper according to one embodiment of the present disclosure in an unfolded and laid flat condition to show an outer surface of the diaper which faces away from the wearer when the diaper is worn.
Figure 5:
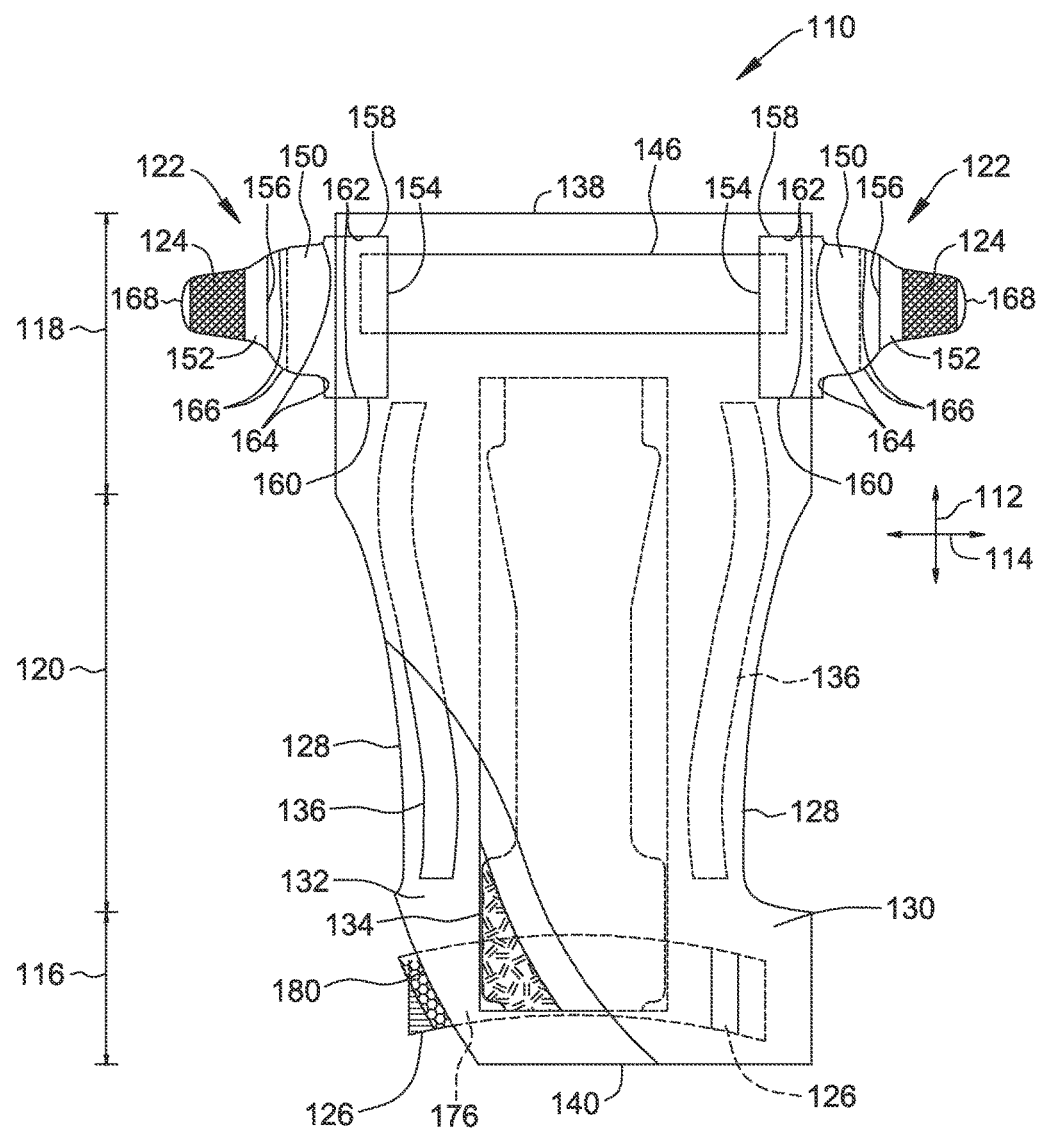
FIG. 5 is a bottom plan view of the diaper of FIG. 4 in an unfolded and laid flat condition to show an inner surface of the diaper which faces towards the wearer when the diaper is worn, portions of the diaper being cut away to illustrate underlying components.

These features will become more apparent with reference to the accompanying drawings. FIGS. 4 and 5 illustrate one suitable embodiment of a diaper (broadly, "an absorbent article"), indicated generally at 110, in an unfolded and laid flat condition to show an outer surface of the diaper which faces away from the wearer when the diaper is worn (FIG. 4) and an inner surface of the diaper which faces the wearer when the diaper is worn (FIG. 5). Portions of the diaper 110 illustrated in FIG. 5 are cut away to illustrate underlying structures. The diaper 110 has a longitudinal direction 112 and a lateral direction 114. While the present description will be made in the context of a diaper 110, it should be understood that the present disclosure is also applicable to other personal care absorbent articles, such as adult incontinence garments, children's training pants, swim pants, and the like.

In one suitable embodiment, the diaper 110 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper 110 can be reusable. That is, the diaper 110 can be intended for multiple uses without departing from some aspects of this disclosure.

In the longitudinal direction 112, the diaper 110 defines a front portion 116, a back portion 118, and a crotch portion 120 extending between and connecting the front portion and the back portion. As used herein, reference to the front portion 116 refers to that part of the diaper 110 which is generally located on the front of a wearer when in use. Reference to the back portion 118 refers to the portion of the diaper 110 generally located at the back of the wearer when in use, and reference to the crotch portion 120 refers to that portion which is generally located between the legs of the wearer when in use.

The diaper 110 includes a bodyside liner 130, an outer cover 132, and an absorbent core 134 located between the bodyside liner and the outer cover. The bodyside liner 130, outer cover 132 and absorbent core 134 collectively define an absorbent assembly. The absorbent assembly can be any suitable shape including, for example, generally I-shaped as illustrated in FIGS. 4 and 5 or generally rectangular.

In the illustrated embodiment, the back portion 118 of the diaper 110 includes a straight back waist edge 138 and the front portion 116 includes a straight front waist edge 140. As used herein, "straight edge" refers to edges that are substantially free from curves, bends, angles, notches, or irregularities. It is understood, however, that the back waist 138 and the front waist 140 may be cut in any suitable shape as are known in the art (e.g., arcuate). As seen in FIGS. 4 and 5, the diaper 110 has opposite longitudinal side edges 128 that extend between the back waist edge 138 and the front waist edge 140. In the illustrated embodiment, each of the side edges 128 includes an arcuate portion for defining a portion of a leg opening during wear of the diaper 110.

The bodyside liner 130 of the diaper 110, as illustrated in FIG. 5, defines a body facing surface that is intended to be worn adjacent and in directed contact with the body of the wearer. The bodyside liner 130 is suitably compliant, soft feeling and nonirritating to the wearer's skin. The bodyside liner 130 is less hydrophilic than the absorbent core 134 and sufficiently porous to be liquid permeable. The bodyside liner 130 can be manufactured from a wide selection of suitable web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably adapted to isolate the wearer's skin from liquids and moisture held by the absorbent core 134.

The outer cover 132 of the diaper 110, which is illustrated in FIG. 4, defines a garment facing surface which is intended to be worn adjacent the clothing of the wearer. In one suitable embodiment, the outer cover 132 is a polyethylene film. In another suitable embodiment, the outer cover 132 comprises a woven or non-woven fibrous web layer which has been totally or partially constructed or treated to impart a desired level of liquid impermeability to selected regions of the outer cover that are adjacent or proximate the absorbent core 134. For example, a clothlike outer cover may be composed of polypropylene spunbond fabric which is laminated and thermally bonded to a stretch-thinned polypropylene film. The outer cover 132 may include a microporous, "breathable" material which permits vapors to escape from diaper 110 while still preventing liquid exudates from passing through. For example, the outer cover 132 may be composed of a microporous polymer film or a nonwoven fabric which has been coated or otherwise treated to impart a desired level of liquid impermeability. The outer cover 132 can also be embossed or otherwise provided with a matte finish to exhibit a more aesthetically pleasing appearance.

The bodyside liner 130 and the outer cover 132 are generally joined in facing relationship with the absorbent core 134 located therebetween. The bodyside liner 130 and the outer cover 132 can be joined to each other around the outer periphery of the diaper 110 by any means known to those skilled in the art such as adhesive bonds, ultrasonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

As mentioned above, the absorbent core 134 is positioned between the bodyside liner 130 and the outer cover 132. The absorbent core 134 is generally conformable and capable of absorbing and retaining liquid body exudates. The absorbent core 134 can include superabsorbent material, staple fibers, binder fibers, and the like, and combinations thereof as is known in the art. The absorbent core 134 may have any of a number of shapes and sizes. For example, the composite absorbent core 134 may be rectangular, I-shaped, or T-shaped. The size and absorbent capacity of the absorbent core 134 should be compatible with the size of the intended wearer and the fluid loading imparted by the intended use of the diaper.

In one suitable embodiment, the diaper 110 may include a surge portion (not shown) disposed between the absorbent core 134 and the bodyside liner 130. The surge portion serves to quickly collect and temporarily hold liquids discharged by the wearer and then release the liquids to the absorbent core 134. Various woven and nonwoven materials can be used to construct the surge portion. For example, the surge portion may be a layer of a spunbonded or meltblown web of polyolefin fibers. The surge portion may also be a bonded carded web of natural and synthetic fibers. The surge portion may be a substantially hydrophobic material and, optionally, can be treated with a surfactant or otherwise to impart a desired level of wettability and hydrophilicity.

The diaper 110 includes a pair of elasticized, longitudinally-extending leg cuffs 136. The leg cuffs 136 are adapted to fit about the legs of a wearer in use and serve as a mechanical barrier to the lateral flow of body exudates. In one suitable embodiment, the leg cuffs 136 can be formed by portions of the outer cover 132, and/or bodyside liner 130, which extend beyond the longitudinal sides of the absorbent core 134. In another suitable embodiment, the leg cuffs 136 can be formed from separate materials (e.g., stands of leg elastics) joined to the outer cover 132 and/or the bodyside liner 130.

The diaper 110 may further include a front waist elastic (not shown) and/or a back waist elastic 146. In the illustrated embodiment, for example, the diaper 110 has a back waist elastic 146 but not a front waist elastic. The back waist elastic 146 is arranged to draw and hold the diaper 110 against the wearer, particularly against the waist of the wearer, as will be more fully discussed.

Materials suitable for use in forming leg cuffs 136 and/or waist elastics 146 are known to those skilled in the art. Examples of such materials are strands or ribbons of a polymeric, elastomeric material which are adhered to the diaper 110 in a stretched position, or which are attached to the diaper while the diaper is pleated, such that elastic constrictive forces are imparted to the diaper. The leg cuffs 136 and/or waist elastics 146 may have any configuration which provides the desired performance. The leg cuffs 136 may be generally straight or optionally curved (as illustrated in FIGS. 4 and 5) to more closely fit the contours of the legs of the wearer. As used herein, "elastic," "elastomeric," and the like refer to the ability of a material or composite to be elongated by at least about 50 percent and upon relaxation to return to within at least 50 percent of its original length.

The leg cuffs 136 and/or waist elastics 146 may be attached to the diaper 110 in any way known to those skilled in the art. For example, the leg cuffs 136 and/or waist elastics 146 may be joined to the diaper 110 by ultrasonic bonding, thermal bonding, adhesive bonding, and the like, and combinations thereof.

The diaper 110 may also include a pair of containment flaps (not shown) that extend longitudinally along the diaper and are adapted to provide a barrier to the lateral flow of body exudates. The containment flaps can be connected to the bodyside liner 130 or other components as is well known in the art. Suitable configurations of the containment flaps 148 are described, for example, in U.S. Pat. No. 5,599,338 issued Feb. 4, 1997, to K. Enloe, the entirety of which is incorporated herein by reference.

As seen in FIGS. 4 and 5, the back portion 118 of the diaper includes a pair of back ears, indicated generally at 122. In one suitable embodiment, the back ears 122 can be formed from extensions of the bodyside liner 130, the outer cover 132, or combinations of both the bodyside liner and the outer cover. In another suitable embodiment, and as illustrated in FIGS. 4 and 5, the back ears 122 can be formed as separate components and attached to the bodyside liner 130, the outer cover 132, or both the bodyside liner and the outer cover as is known in the art. In the illustrated embodiment, the back ears 122 are attached to the body-facing surface of the bodyside liner 130 such that the attached portion of the ears 122 are disposed between the wearer's body and bodyside liner when the diaper 110 is worn.

In one suitable embodiment, each of the back ears 122 includes an elastomeric portion 150, a non-elastomeric portion 152, and a primary first fastening component 124 mounted to the non-elastomeric portion (FIG. 5). As seen in FIG. 5, each of the elastomeric portions 150 has a proximal edge 154, an opposed distal edge 156, an upper edge 158, and a lower edge 160. The proximal edge 154 of each of the elastomeric portions 150 is spaced inward from the respective side edge 128 of the diaper 110 such that a portion of the elastomeric portion overlaps the bodyside liner 130. The part of each of the elastomeric portions 150 overlapping the bodyside liner 130 is bonded (e.g., adhesive bonding, thermal bonding, both thermal and adhesive bonding) to at least the bodyside liner. In another suitable embodiment, the elastic component 150 may be eliminated and the entire back ear 122 may be constructed from the non-elastic component 152.

In the embodiment illustrated in FIGS. 4 and 5, the proximal edge 154 and the distal edge 156 of each of the elastomeric portions 150 are generally parallel with respect to each other, and both are straight (i.e., linear). In one suitable embodiment, the proximal edge 154 has a length from about 2 inches (5.1 centimeters) to about 7 inches (17.8 centimeters), preferably from about 3 inches (7.6 centimeters) to about 6 inches (15.2 centimeters), and more preferably from about 3.5 inches (8.9 centimeters) to about 5.5 inches (14.0 centimeters). The distal edge 156 has a length from about 0.25 inch (0.635 centimeter) to about 6 inches (15.24 centimeters), and preferably from about 1 inch (2.54 centimeters) to about 3 inches (7.6 centimeters). Further, the ratio of the length of the distal edge 156 to the proximal edge 154 is suitably from about 1:28 to about 3:4, and, and preferably from about 1:10 to about 2:3, and more preferably from about 1:4 to about 1:2.

Both the upper and lower edges 158, 160 have first segments 162 that are generally parallel to each other and generally perpendicular to the respective proximal edges 154. Each of the first segments 162 generally correspond to the part of each of the elastomeric portions 150 that overlap the bodyside liner 130. In the illustrated embodiment, the first segments 162 of the upper edges 158 of the elastomeric portion 150 are spaced from the back waist edge 138. It is understood, however, that the first segments 162 can be aligned with the back waist edge 138 of the diaper 110.

Second segments 164 of each of the upper and lower edges 158, 160 are generally coaxial and extend towards each other generally perpendicular to the first segments 162. In the illustrated embodiment, the second segment 164 of the lower edge 160 has a length greater than the length of the second segment of the upper edge 158. It is understood, however, that the second segments 164 of the upper and lower edges 158, 160 can have any suitable length.

Each of the illustrated elastomeric portions 150 further includes an arcuate third segment 166 interconnecting the second segments 164 to the respective distal edge 156. In the illustrated embodiment, the third segments 166 are generally mirror images of each other. It is understood, however, that the third segments 166 can have any suitable shape and that the third segments of the upper edges 158 can have a shape that is different that the shape of the third segments of the lower edges 160.

The elastomeric portions 150 of the back ears 122 can be formed from any type of elastomeric material capable of performing as described herein. In one suitable embodiment, the elastomeric material will be stretchable in at least one direction (e.g., in the lateral direction 114 of the diaper 110 as viewed in FIGS. 4 and 5) and alternatively, the elastomeric material will be stretchable in two directions (e.g., in both the longitudinal direction 112 and the lateral direction of the diaper as viewed in FIGS. 4 and 5). Suitably when the elastomeric material is stretchable in a single direction, the stretch direction of the elastomeric material will be oriented so as to provide elastomeric forces which tend to pull the front and rear portions of the article towards one another such that the article is maintained about the waist of a wearer.

In one suitable embodiment, the elastomeric material from which the elastomeric portions 150 of the back ears 122 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 150 of the back ears 122 can be formed from a stretch-bonded-laminate (SBL) material, a neck-bonded-laminate (NBL) material, an elastomeric film, an elastomeric foam material, or the like.

Each of the non-elastomeric portions 152 of the back ears 122 is attached to a respective one of the elastomeric portions 150, and the primary first fastening components 124 (such as a hook material) are in turn disposed on the non-elastomeric portions. As illustrated in FIGS. 4 and 5, the non-elastomeric portions 152 of the back ears 122 extend in part transversely outward of the respective elastomeric portion 150 and the primary first fastening component 124 of each of the non-elastomeric portions are configured for engaging a loop component disposed in the front waist region 116 of the diaper 110 in the wear configuration, as will be discussed more fully.

As seen best in FIG. 5, each of the illustrated non-elastomeric portions 152 further comprise a grip region 168 transversely outward of the primary first fastening component 124 for use in manually gripping and manipulating the non-elastomeric portion and more broadly the respective back ear 122 relative to the diaper 110. The grip region 168 is non-attachable to the diaper 110. The term "non-attachable" as used in this instance means that the grip region 168 is not releasably or otherwise removably attachable to the diaper 110. In one embodiment, the grip region 168 extends transversely outward from the respective primary first fastening component 124 a distance of at least about 1 mm, such as in the range of about 1 mm to about 10 mm to provide sufficient unattached material for readily gripping and pulling on the non-elastomeric portion 152.

Figure 6:
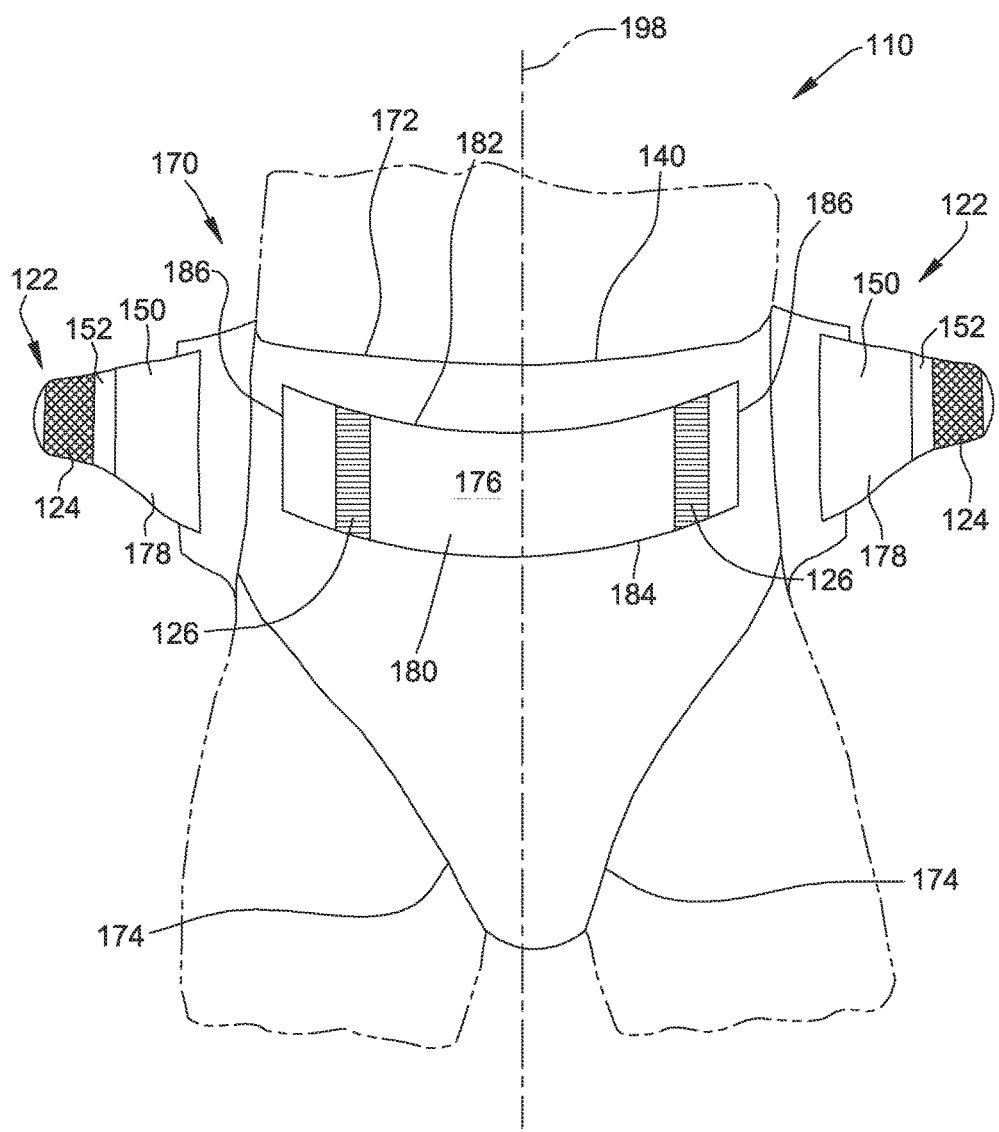
FIG. 6 is a front view of the diaper of FIG. 4 in a wear configuration and donned by a wearer with the fastening system unfastened.
Figure 7:
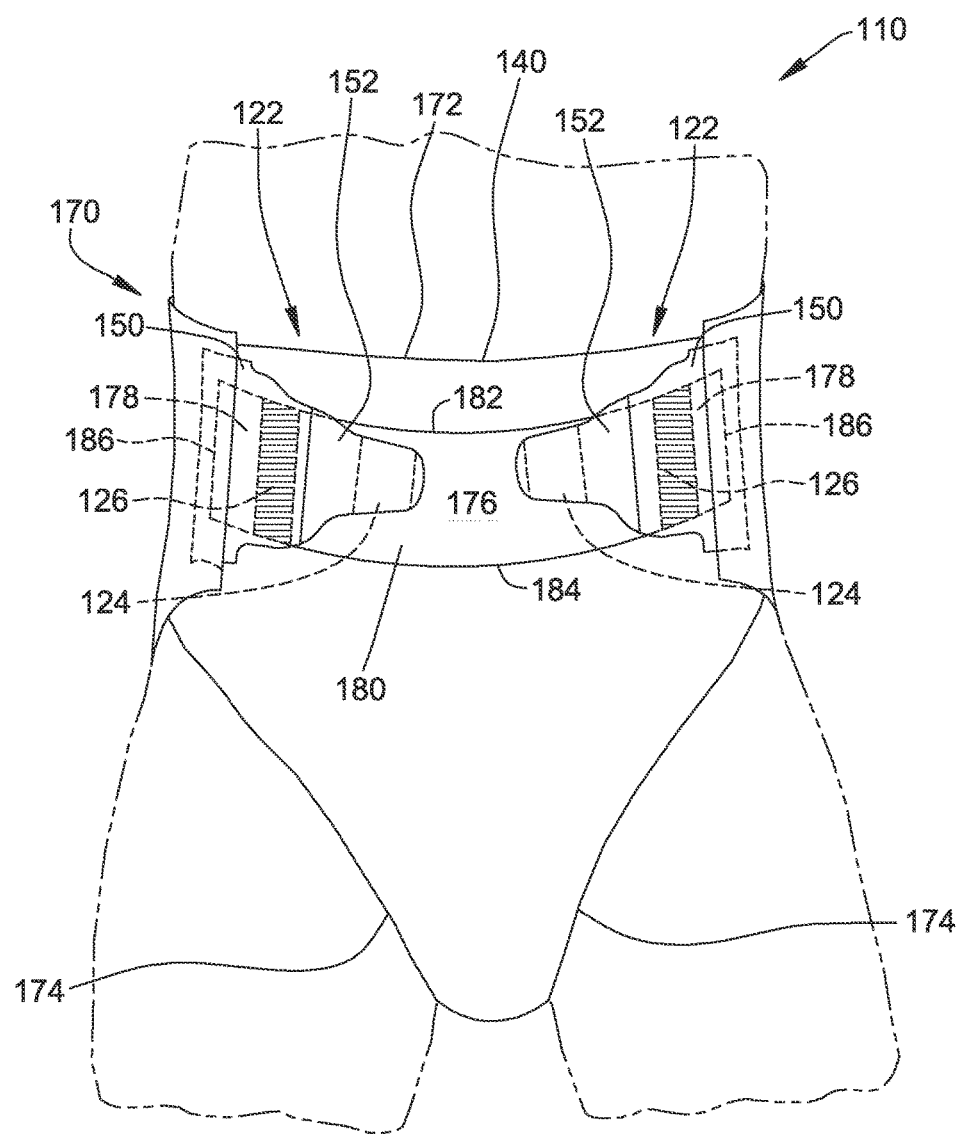
FIG. 7 is a front view of the diaper of FIG. 4 in a wear configuration and donned by a wearer with the fastening system fastened.

The diaper 110 can be selectively moved from the unfastened configuration, as illustrated in FIGS. 4 and 5, to a fastened or wear configuration as illustrated in FIGS. 6 and 7, by attaching the back waist region 118 (and more specifically the back ears 122) to the front waist region 116 using an article fastening system, which is indicated generally at 170, to define a three-dimensional wear configuration of the diaper having a waist opening 172 and a pair of leg openings 174. Although the diaper 110 illustrated in FIGS. 6 and 7 shows the back waist region 118 (and more specifically the back ears 122) overlapping the front waist region 116 upon connection thereto, which is convenient, the diaper can also be configured so that the front waist region overlaps the back waist region when connected.

According to some embodiments, the article fastening system 170 comprises a primary fastening system and a secondary fastening system. The primary fastening system comprises the primary first fastening components 124 disposed on the non-elastomeric portions 152 of the back ears 122 and at least one corresponding primary second fastening component 176 which is adapted for refastenable engagement to the primary first fastening components. In one suitable embodiment, an outer surface of each of the primary fastening components 124, 176 comprises a plurality of engaging elements. More specifically, the engaging elements of the primary first fastening components 124 are adapted to repeatedly engage and disengage corresponding engaging elements of the primary second fastening components 176 to releasably secure the diaper 110 in its wear configuration.

The primary fastening components 124, 176 may comprise any refastenable fasteners suitable for absorbent articles, such as adhesive fasteners, cohesive fasteners, mechanical fasteners, or the like. In one suitable embodiment, the primary fastening components 124, 176 comprise mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage such as open cell foam or the like, etc. Other suitable mechanical fastening components include male and/or female mating components, buckles, snaps, or the like. In the illustrated embodiment, the primary first fastening components 124 comprise hook fasteners and the primary second fastening components 176 comprise a complementary loop fastener disposed on the outer surface of the outer cover 132. Alternatively, the primary first fastening components 124 may comprise loop fasteners and the primary second fastening components 176 may comprise complementary hook fasteners.

The shape, density, and polymer composition of the hooks and loops may be selected to obtain the desired level of engagement between the primary fastening components 124, 176. A more aggressive hook material may comprise a material with a greater average hook height and/or a greater percentage of directionally-aligned hooks.

In some embodiments, the outer surface of the outer cover 132 of the diaper 110 is suitably constructed to define the primary second fastening component 176, which is a loop fastener. That is, the outer cover 132 itself can be formed of a material that defines the primary second fastening component 176 (e.g., a suitable non-woven material).

In one suitable embodiment, and as illustrated in FIGS. 5-7, the primary second fastening component 176 can be formed as a separate component and attached to the outer surface of the diaper's outer cover 132. More specifically, a strip, indicated generally at 180, comprising loop fastening material is attached to the front waist region 116 of the diaper. The strip 180, as seen in FIG. 6, comprises an arcuate upper edge 182, an arcuate lower edge 184, and a pair of side edges 186 connecting the upper and lower edges 182, 184. As a result, the strip 180 itself is non-linear and, more specifically, arcuate in shape.

Figure 8:
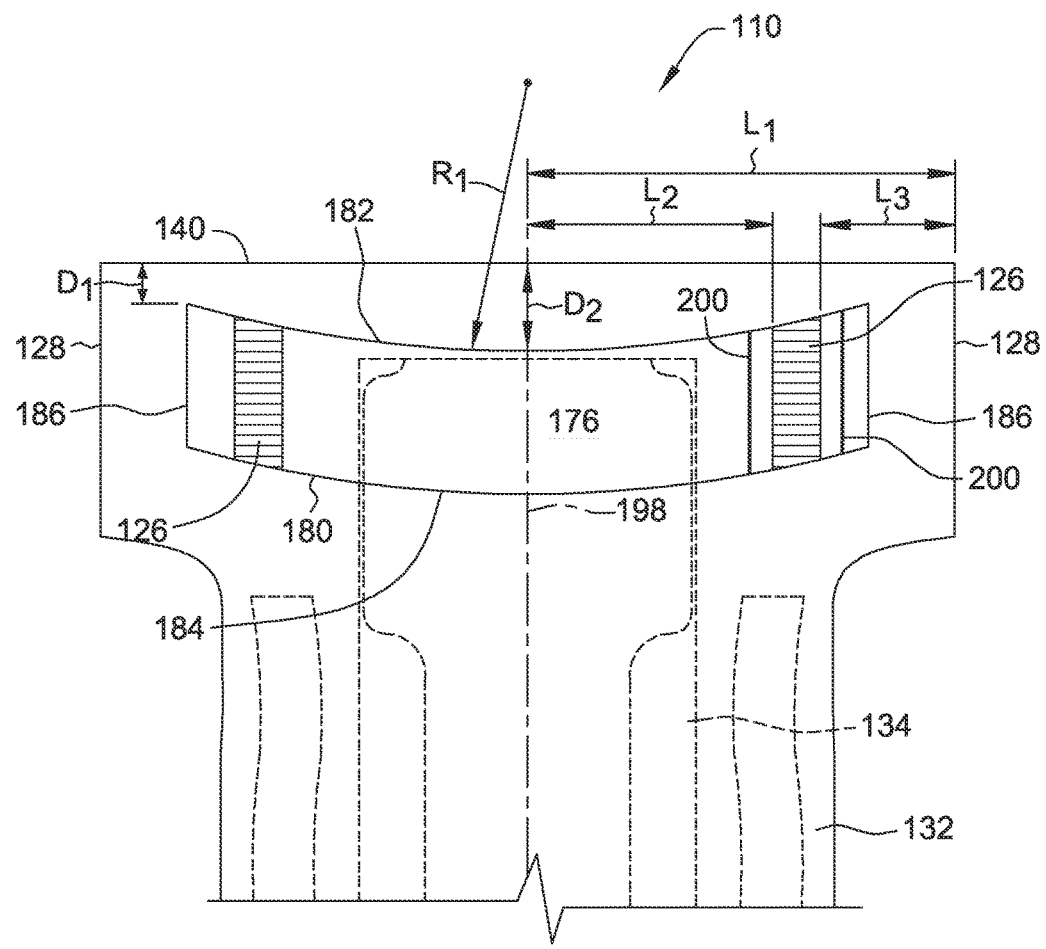
FIG. 8 is an enlarged, fragmented top plan view of a portion of the diaper of FIG. 4 illustrating relative distances from a center line to various components of the diaper.

With reference now to FIG. 8, the upper edge 182 of the illustrated embodiment of the strip 180 is spaced from the front waist edge 140 a first (or minimum) distance D1 adjacent each of the side edges 186 and a second (or maximum) distance D2 spaced inboard from each of the side edges, which is greater than the first distance. In the illustrated embodiment, the first distance D1 is taken along lines that are coaxially aligned with one of the side edges 186 of the strip 180. It is understood, however, that in other suitable embodiments, the first distance D1 can be offset (i.e., inboard) from the side edge 186 without departing from some aspects of this disclosure. Also in the illustrated embodiment, the second distance D2 is taken along a center line 198 of the diaper 110, which is coaxially aligned with the longitudinal axis of the diaper 110. It is understood, however, that in other suitable embodiments, the second distance D2 can be offset from the center line 198 of the diaper 110 without departing from some aspects of this disclosure.

In one suitable embodiment, the first distance D1 (i.e., the minimum distance the upper edge 182 of the strip 180 is spaced from the front waist edge 140) can be between 3 mm and 30 mm, and the second distance D2 (i.e., the maximum distance the upper edge 182 of the strip 180 is spaced from the front waist edge 140) can be between 6 mm and 67 mm. It is understood, however, that the first distance D1 and the second distance D2 can be any suitable distance without departing from some aspects of this disclosure.

As illustrated in FIG. 8, the arcuate upper edge 182 of the strip 180 is defined by a suitable radius R1. In one suitable embodiment, the radius R1 is between 155 mm and 1,740 mm, more particularly, between 400 mm and 1,400 mm, and even more particularly between 600 mm and 1,200 mm. In the illustrated embodiment, for example, the radius R1 is approximately 700 mm. It is contemplated that the arcuate upper edge 182 of the strip 180 can have more than a single radius. That is, portions of the upper edge 182 can have different radii. It is further contemplated that in some suitable embodiments, the upper edge 186 can be other than arcuate, including straight, without departing from some aspects of this disclosure.

In the illustrated embodiment, the arcuate upper edge 182 and the arcuate lower edge 184 have the same shape. Thus, the radius R1 of the upper edge 182 is the same as the radius of the lower edge 184. It is contemplated, however, that is other suitable embodiments, the lower edge 184 can have a shape that is different that the shape of the upper edge. That is, the lower edge 184 can have a radius that is different than the radius R1 of the upper edge 182. It is further contemplated that the lower edge 184 can be other than arcuate, including straight, without departing from some aspects of this disclosure.

In the illustrated embodiment, the side edges 186 of the strip 180 are spaced from the respective side edges 128 of the diaper 110. It is contemplated, however, that in other suitable embodiments, the side edges 186 of the strip 180 can be aligned with the side edges 128 of the diaper 110. In such an embodiment, the first distance D1 can be taken along a line that is coaxially aligned with at least a portion of the side edges 128 of the diaper 110.

With reference again to FIGS. 4-7, the secondary fastening system of the article fastening system 170 comprises a pair of secondary first fastening components 126 and a complimentary pair of secondary second fastening components 178. The secondary first fastening components 126 are disposed on the front portion 116 of the diaper 110 and are adapted for refastenable engagement to at least one corresponding secondary second fastening component 178 (e.g., the elastomeric portion 150 of the back ears 122).

As best seen in FIGS. 4 and 8, the strip 180 may comprise the pair of spaced-apart secondary first fastening components 126. In the illustrated embodiment, for example, the secondary first fastening components 126 comprise hook fasteners and are configured to engage the secondary second fastening components 178, which are defined by the elastomeric portions 150 of the back ears 122, in the wear configuration of the diaper 110. Again, as used herein "hook" fasteners refers broadly to any suitable mechanical fastener adapted to engage loop components including, e.g., hooks, bulbs, mushrooms, arrowheads, balls on stems, stems, structures having stems that engage such as open cell foam or the like, etc. In one embodiment, the secondary first fastening components 126 may be constructed of polyethylene or other suitable polymer blends.

In one suitable embodiment, the elastomeric portions 150 of the back ears 122 are constructed so at least the inner surfaces of the elastomeric portions define the secondary second fastening components 178 in the form of loop fastening components (i.e., the elastomeric portions and the respective secondary second fastening components are formed integrally). The elastomeric portions 150 in one suitable embodiment can be constructed of NBL material so that the elastomeric portions itself defines a loop fastening component. In another suitable embodiment, the elastomeric portions 150 can be constructed of VFL material so that the elastomeric portions itself defines a loop fastening component. It is understood, however, that the secondary second fastening components 178 may be formed separate from the elastomeric portions 150 and attached thereto, such as by adhesive, thermal bonds, ultrasonic bonds, pressure bonds, or other suitable techniques without departing from the scope of this disclosure.

In other suitable embodiments, the secondary first fastening components 126 may comprise loop fasteners and the secondary second fastening components 178 may comprise hook fasteners. Further, in some embodiments, the secondary first fastening components 126 may be a single, integral fastener. For example, in one suitable embodiment the secondary first fastening components 126 may be a single, loop fastener, and the secondary second fastening components 178 may be hook fasteners.

In one suitable embodiment and as seen in FIGS. 4 and 8, the strip 180 comprises both the secondary first fastening components 126 of the secondary fastening system and the primary second fastening component 176 of the primary fastening system. In one such embodiment wherein the primary second fastening component 176 comprises a loop material and the secondary first fastening component 126 comprises a hook material, the strip 180 may be a suitable loop material (forming the primary second fastening component), and then the hook material may be extruded onto the loop material at two or more locations forming the secondary first fastening components.

In another suitable embodiment, the secondary first fastening components 126 can be formed separate from the primary second fastening component 176. In such an embodiment, the primary second fastening component 176 can be formed to define the strip 180 and the secondary first fastening components 126 can be attached in overlaying relationship with portions of the primary second fastening component. In such embodiments, the secondary first fastening components 126 may be attached to the strip 180 and/or the primary second fastening component 176 using any suitable means known to those skilled in the art, including, e.g., adhesive bonds, ultrasonic bonds, thermal bonds, pressure bonds, and the like, and combinations thereof.

In some embodiments, the secondary first fastening components 126 may be attached to the diaper 110 and/or the strip 180 after the strip has been attached to the diaper 110. For example, in one suitable embodiment the strip 180 may be first bonded to the diaper 110 using any suitable means as discussed, and then the secondary first fastening components 126 may be bonded to or extruded on the strip. In other embodiments, the strip 180 comprising both the secondary first fastening components 126 and primary second fastening components 176 can be attached to the diaper 110 as one single unit.

According to some embodiments, the secondary first fastening components 126 and/or the strip 180 may be sufficiently bonded to the diaper 110 such that a shear force exerted on the secondary first fastening components and/or the strip during use of the diaper does not cause the secondary first fastening components and/or the strip to loosen or completely disengage from the diaper. For example, in some embodiments, an improved adhesive or the like can be used such that the secondary first fastening components 126 and/or the strip 180 remain securely fastened to, e.g., the outer cover despite the forces exerted on the fastening system 170 during use. In such embodiments, the diaper 110 may be less prone to pop-opens and the edges of the secondary first fastening components 126 and/or the strip 180 may remain flush with the outer cover 132 thus reducing irritation during wear which may otherwise be caused by a loose secondary first fastener and/or a loose strip.

When the diaper 110 is moved to the wear configuration with the primary fastening components 124, 176 engaging one another, the secondary fastening components 126, 178 may also engage one another in order to provide increased stability and leakage protection (FIGS. 6 and 7). For example, because the article fastening system 170 comprises four engagement points, the diaper 110 will be less prone to pop-opens when worn. Further, because the secondary fastening components 126, 178 engage each other closer to a side of a wearer than an engagement point of the primary fastening components 124, 176, the secondary fastening system secures the diaper 110 nearer the wearer's sides and legs thus reducing leakage near the leg openings 174 of the diaper. Still further, and again because the secondary fastening components 126, 178 engage each other near a side of the wearer, the secondary fastening system may provide increased stability, thus reducing the occurrence of, e.g., sagging of the diaper due to movement of the wearer. Moreover, as a result of the strip 180 having arcuate upper and lower edges 182, 184, the secondary first fastening components 126 are located in spaced relationship from the respective leg opening 174 when the diaper 110 is donned by the wearer. As a result, the secondary first fastening components 126 do not rub against or otherwise contact the skin of the wearer during use. Accordingly, the secondary first fastening components 126 of the present disclosure are less likely to cause the wearer skin irritation or red marking.

One suitable placement of the secondary first fastening components 126 in relation to other components of the diaper 110 in order to achieve one or more of the described benefits may be more readily understood with reference again to FIG. 8. For example, L1 indicates a distance of the outer edge 128 of the diaper 110 from the center line 198 which is coaxially aligned with the longitudinal axis of the diaper 110; L2 indicates a distance of an inboard edge of one of the secondary first fastening components 126 from the center line; and L3 indicates a distance from an outboard edge of the secondary first fastening component 126 to the outer edge of the diaper. Thus, the width (as measured in the lateral direction 114 of the diaper 110) of the secondary first fastening component 126 can be readily determined by subtracting the distance L2 and L3 from L1.

In some embodiments, a ratio of L2:L1, L2:L3, and/or L1:L3 may be appropriately configured such that the diaper 110 exhibits one or more of the benefits described herein. For example, in some embodiments, the diaper may be constructed such that the ratio of L2:L1 (i.e., the ratio of a distance from the center line 198 to an inboard edge of the secondary first fastening component 126 compared to a distance from the center line to the outer edge 128 of the front portion 116 of the diaper 110) is at least 0.50 and less than 1.00. Preferably, the diaper 110 may be constructed such that the ratio of L2:L1 is between 0.50 and 0.80, and more preferably between 0.50 and 0.70, and even more preferably between 0.50 and 0.65.

Further, in some embodiments, the diaper 110 may be constructed such that the ratio of L2:L3 (i.e., the ratio of the distance from the center line 198 to the inboard edge of the secondary first fastening component 126 compared to a distance from the outboard edge of the secondary first fastening component 126 to the outer edge 128 of the diaper 110) is greater than 1.15. Preferably, the diaper 110 may be constructed such that the ratio of L2:L3 is between 1 and 10, and more preferably between 1.1 and 5, and even more preferably between 1.15 and 2. As a result, each of the secondary first fastening components 126 is disposed, in their entireties, in closer proximity to the side edges 128 of the diaper 110 than to the center line 198 of the diaper 110.

With reference still to FIG. 8, the bold lines 200 adjacent each of the inboard and outboard edges of one of the secondary first fastening components 126 seen in FIG. 8 indicate an appropriate range on the front portion 116 of the diaper 110 in which the secondary first fastening components can be disposed according to some embodiments of the present disclosure. That is, the secondary first fastening component 126 can be disposed anywhere within the range. In the illustrated embodiment, the secondary first fastening component 126 has a width substantially less (e.g., about 50%) of the width of the range. It is contemplated, however, that the secondary first fastening component 126 can have any suitable width. Thus, the width of the secondary first fastening component 126 can be wider or narrower than illustrated in FIG. 8. Although the bold lines 200 are depicted only on the right side (as viewed in FIG. 8) of the front portion 116 of the diaper 110, one skilled in the art will appreciate that the diaper may be symmetrical about its center line 198 such that the secondary first fastening component 126 disposed on the left side of the front portion of the diaper will be disposed in a substantially similar range from the center line 198.

Figure 9:
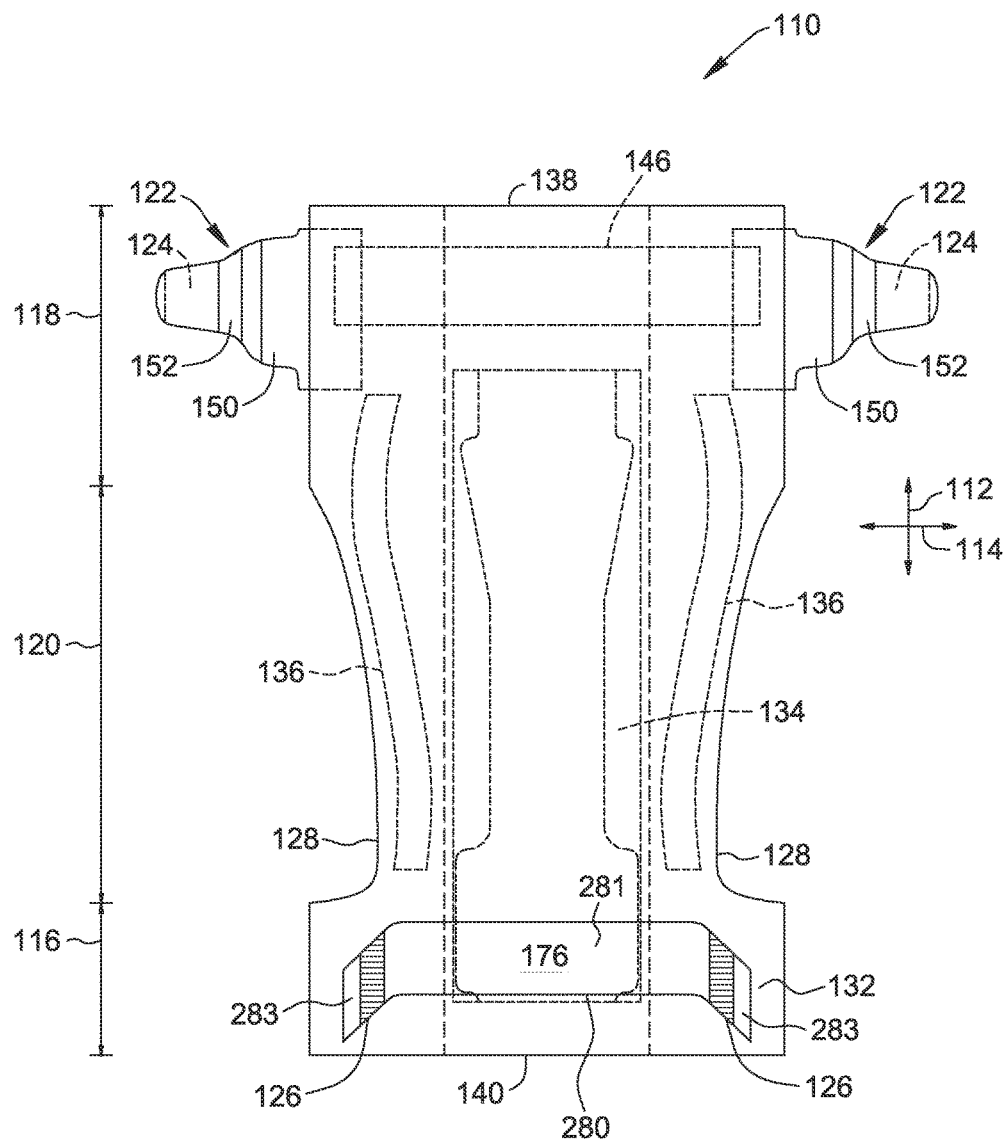
FIG. 9 is a top plan view of a diaper according to another embodiment in an unfolded and laid flat condition to show an outer surface of the diaper which faces away from the wearer when the diaper is worn.

Turning now to FIG. 9, another suitable embodiment of the diaper 110 according to some aspects of the disclosure is illustrated. Specifically, FIG. 9 depicts the diaper 110 in an unfolded and laid flat condition to again show the outer surface of the diaper which faces away from the wearer when the diaper is worn. In the depicted embodiment, the majority of the operable aspects of the diaper 110 are the same or substantially similar to the embodiment depicted in FIGS. 4-8 and as described herein. However, a strip 280 of this embodiment is not arcuate but rather comprises a generally straight central portion 281 and a pair of angled portions 283 with each of the angled portions flanking opposite sides of the straight portion. As seen in FIG. 9, each of the angled portions 283 of the strip 280 angle upward and outward from a respective side of the straight portion 281 towards the front waist edge 140 and the respective side edge 128 of the diaper 110. It is contemplated, however, that the strip 280 can have any suitable shape (e.g., chevron or V-shaped, U-shaped) without departing from some aspects of this disclosure.

Figure 10:
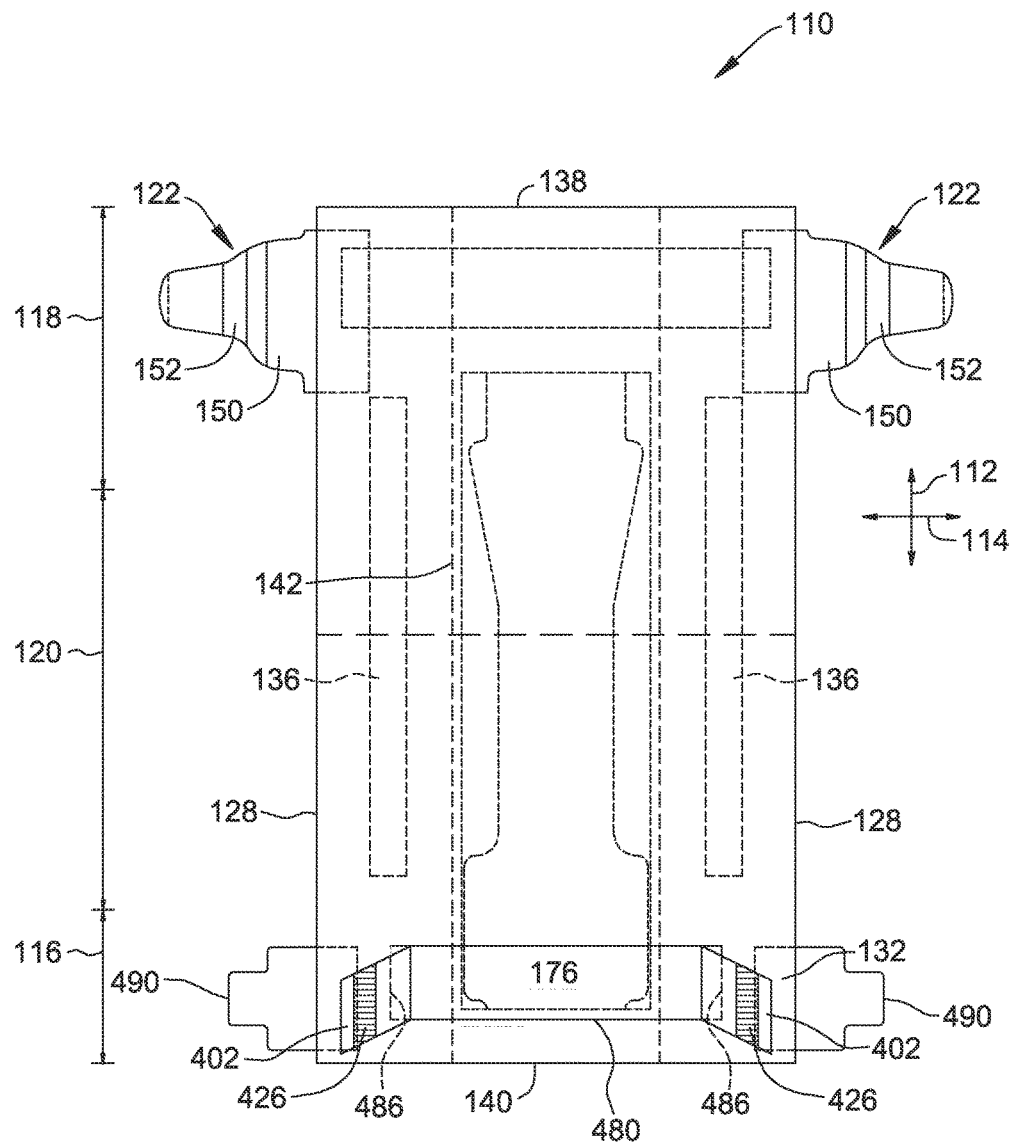
FIG. 10 is a top plan view of a diaper according to still another embodiment in an unfolded and laid flat condition to show an outer surface of the diaper which faces away from the wearer when the diaper is worn.

FIG. 10 illustrates yet another suitable embodiment of the diaper 110 according to some aspects of the disclosure. FIG. 10 depicts the diaper 110 in an unfolded and laid flat condition to show the outer surface of the diaper which faces away from the wearer when the diaper is worn. The majority of the operable aspects of the diaper 110 are the same or substantially similar to the embodiment depicted in FIGS. 4-8.

However, in this embodiment, each of a pair of secondary first fastening components 426 are provided on a corresponding carrier 402 which is then attached to or otherwise provided on the outer cover 132. In this embodiment, the side edges 486 of the strip 480 are disposed inboard of the secondary first fastening components 426. However, rather than attaching or otherwise providing the secondary first fastening components 126 directly to the outer cover 132, each secondary first fastening component is intermediately attached to a respective carrier 402 which is then attached to the outer cover 132. The secondary first fastening components 426 are disposed in closer proximity to the front waist edge 140 than the strip 480.

The front portion 116 of the diaper 110 illustrated in FIG. 10 includes a pair of front ears 490. In one suitable embodiment, the front ears 490 can be formed from extensions of the bodyside liner 130, the outer cover 132, or combinations of both the bodyside liner and the outer cover. In another suitable embodiment, and as illustrated in FIG. 10, the front ears 490 can be formed as separate components and attached to the bodyside liner 130, the outer cover 132, or both the bodyside liner and the outer cover as is known in the art. In the illustrated embodiment, the front ears 490 are attached to the body-facing surface of the bodyside liner 130 such that the attached portion of the ears 490 are disposed between the wearer's body and bodyside liner when the diaper 110 is worn. The front ears 490 can be made from any suitable material including SMS and other suitable non-wovens.

Figure 11:
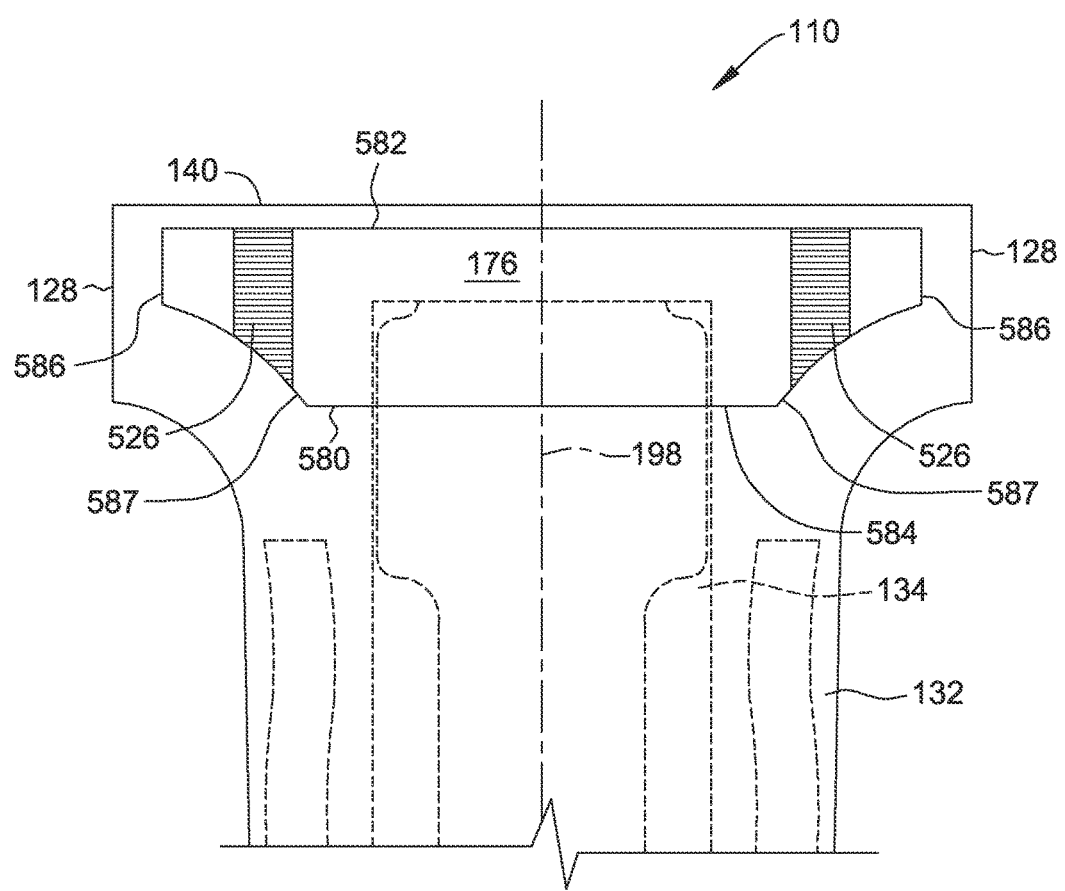
FIG. 11 is an enlarged, fragmented top plan view of a diaper according to still yet another embodiment in an unfolded and laid flat condition to show an outer surface of the diaper which faces away from the wearer when the diaper is worn.

FIG. 11 illustrates yet another suitable embodiment of the diaper 110 according to some aspects of the disclosure. Once again, FIG. 11 depicts the diaper 110 in an unfolded and laid flat condition to show the outer surface of the diaper which faces away from the wearer when the diaper is worn. The majority of the operable aspects of the diaper 110 seen in FIG. 11 are the same or substantially similar to the embodiment depicted in the FIGS. 4-8.

However, in this embodiment, a strip 580 comprising the primary second fastening component 176 and a pair of secondary first fastening components 526 is attached to the front waist region 116 of the diaper 110. The strip 580, as seen in FIG. 11, comprises a straight upper edge 582, a straight lower edge 584, and a pair of side edges 586. The strip 580 of this embodiment further includes a pair of spaced-apart arcuate cutouts 587 disclosed adjacent respective side edges 586 of the strip. Suitably, the cutouts 587 extend through the secondary first fastening components 526 such that the lower edges of the components and strip 580 are coterminous.

In one suitable embodiment and as seen in FIG. 11, the arcuate cutouts 587 have approximately the same radius as an adjacent portion of the side edges 128 of the diaper 110 (i.e., a portion of the side edges 128 that partially define the leg openings 174 during use). It is understood that the arcuate cutouts 587 can have different radii compared to the adjacent portion of the side edges 128 of the diaper 110 without departing from some aspects of this invention. It is also understood that embodiments having front ears (such as the front ears 490 illustrated in FIG. 10) wherein the strip and more specifically the secondary first fastening components 526 extend onto the ear, the arcuate cutouts 587 can have approximately the radius as an adjacent portion of the respect front ear.

Figure 12:
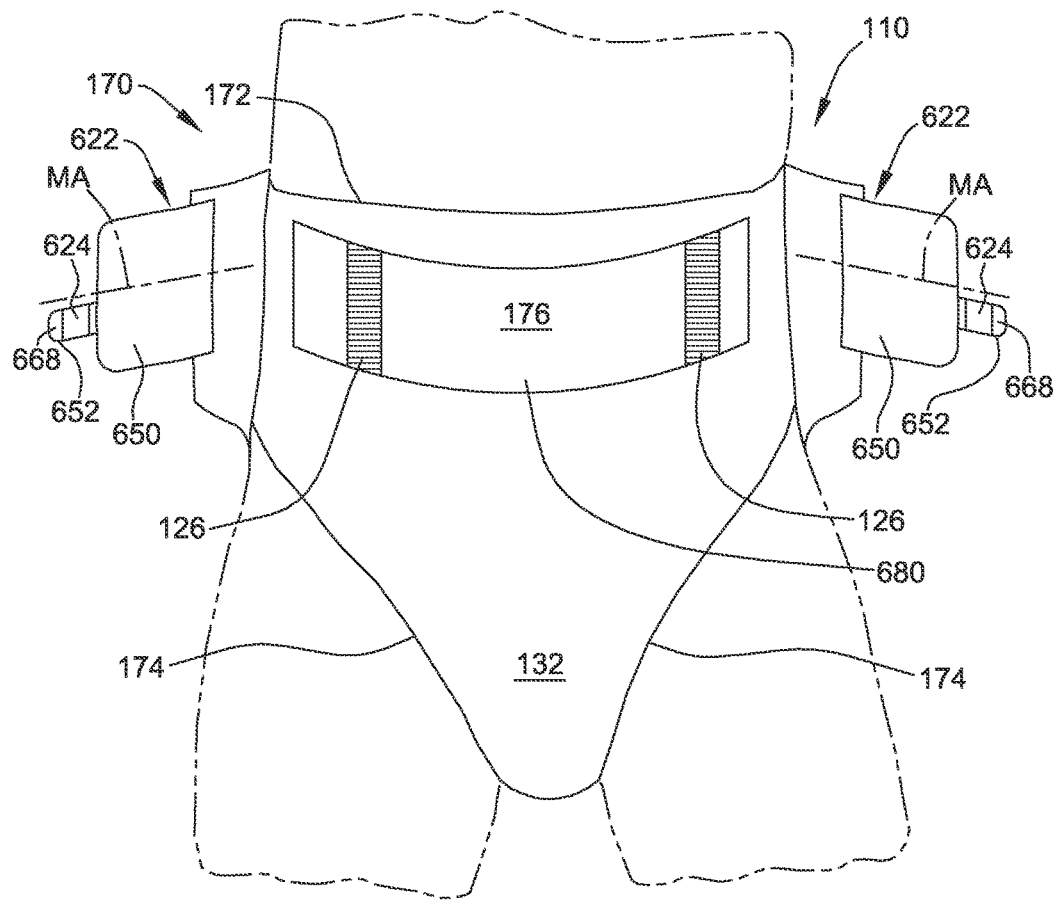
FIG. 12 is a front view of a diaper of another suitable embodiment in a wear configuration and donned by a wearer with the fastening system unfastened.
Figure 13:
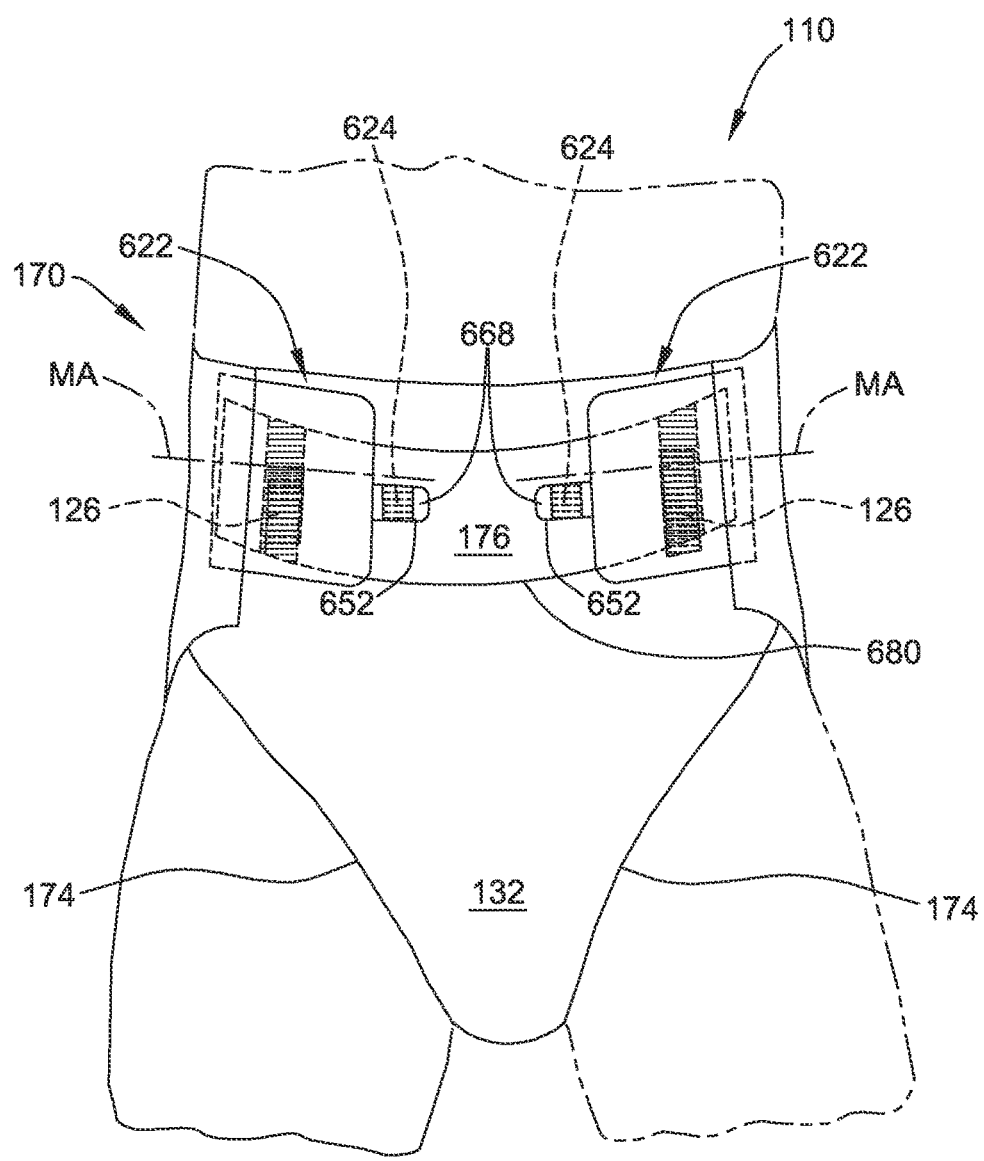
FIG. 13 is a front view of the diaper of FIG. 12 in a wear configuration and donned by a wearer with the fastening system fastened.

FIGS. 12 and 13 illustrate another suitable embodiment of the diaper 110 according to some aspects of the disclosure. The majority of the operable aspects of the diaper 110 seen in FIGS. 12 and 13 are the same or substantially similar to the embodiments depicted in the FIGS. 4-8. In this embodiment, however, the diaper 110 includes a pair of back ears, indicated generally at 622, having another suitable embodiment. Each of the back ears 622 includes an elastomeric portion 650, a non-elastomeric portion 652, and a primary first fastening component 624 mounted to the non-elastomeric portion (FIG. 12).

The elastomeric portions 650 of the back ears 622 can be formed from any type of elastomeric material capable of performing as described herein. In one suitable embodiment, the elastomeric material will be stretchable in at least one direction (e.g., in the lateral direction 114 of the diaper 110) and alternatively, the elastomeric material will be stretchable in two directions (e.g., in both the longitudinal direction 112 and the lateral direction of the diaper). Suitably when the elastomeric material is stretchable in a single direction, the stretch direction of the elastomeric material will be oriented so as to provide elastomeric forces which tend to pull the front and rear portions of the article towards one another such that the article is maintained about the waist of a wearer.

In one suitable embodiment, the elastomeric material from which the elastomeric portions 650 of the back ears 622 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 650 of the back ears 622 can be formed from a stretch-bonded-laminate (SBL) material, a neck-bonded-laminate (NBL) material, an elastomeric film, an elastomeric foam material, or the like.

Figure 14:
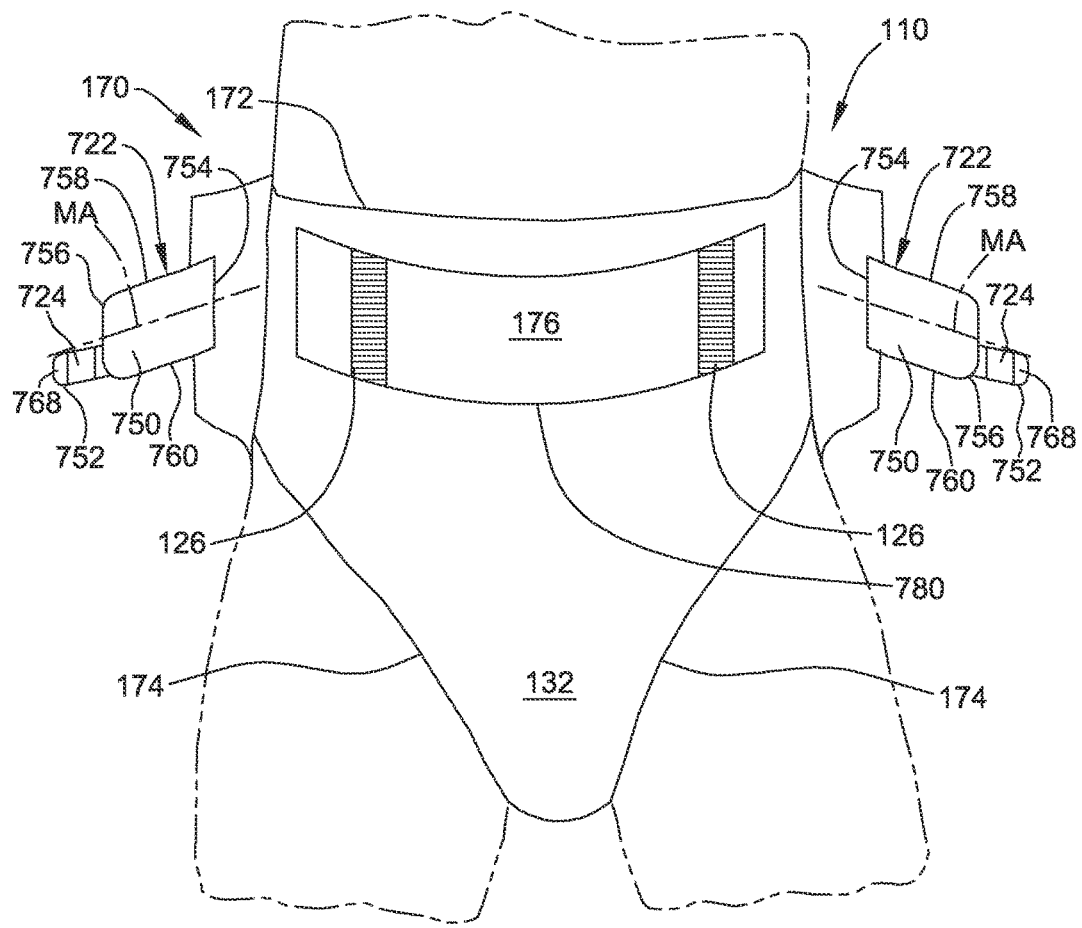
FIG. 14 is a front view of a diaper of yet another suitable embodiment in a wear configuration and donned by a wearer with the fastening system unfastened.

Each of the non-elastomeric portions 652 of the back ears 622, which in this embodiment are tabs, is attached to a respective one of the elastomeric portions 650, and the primary first fastening components 624 (such as a hook material) are in turn disposed on the non-elastomeric portions. As illustrated in FIGS. 13 and 14, the non-elastomeric portions 652 of the back ears 622 extend in part transversely outward of the respective elastomeric portion 650 and the primary first fastening component 624 of each of the non-elastomeric portions are configured for engaging a loop component (e.g., the primary second fastening component 176) disposed in the front waist region 116 of the diaper 110 in the wear configuration.

With reference to FIG. 12, each of the elastomeric portions 650 of the back ears 622 have a medial line MA that divides the elastomeric portion into an upper half and a lower half. In the illustrated embodiment and as seen in FIG. 12, the non-elastomeric portions 652 extend from the lower half (i.e., below the medial line MA) of each of the elastomeric portions 650 such that the entire non-elastomeric portion is disposed below the medial line. That is, no portion of the non-elastomeric portion 652 is disposed above the medial line MA of the elastomeric portion 650. In this embodiment, the medial line MA extends through the midpoint of both the proximal and distal edges of the respective elastomeric portions 650.

As seen best in FIG. 12, each of the illustrated non-elastomeric portions 652 further comprise a grip region 668 transversely outward of the primary first fastening component 624 for use in manually gripping and manipulating the non-elastomeric portion and more broadly the respective back ear 622 relative to the diaper 110. The grip region 668 is non-attachable to the diaper 110. In one embodiment, the grip region 668 extends transversely outward from the respective primary first fastening component 624 a distance of at least about 1 mm, such as in the range of about 1 mm to about 10 mm to provide sufficient unattached material for readily gripping and pulling on the non-elastomeric portion 652.

The diaper 110 can be selectively moved from the unfastened configuration, as illustrated in FIG. 12, to a fastened or wear configuration as illustrated in FIG. 13, by attaching the back ears 622 to the front waist region 116 using the article fastening system 170 to define a three-dimensional wear configuration of the diaper having a waist opening 172 and a pair of leg openings 174. The article fastening system 170 illustrated in FIGS. 12 and 13 comprises a primary fastening system and a secondary fastening system. The primary fastening system comprises the primary first fastening components 624 disposed on the non-elastomeric portions 652 of the back ears 622 and at least one corresponding primary second fastening component 176 which is adapted for refastenable engagement to the elastomeric portion 650.

In this embodiment, a strip 680, which is substantially similar to the strip 180 seen in FIGS. 6 and 7, comprising the primary second fastening component 176 and the secondary first fastening components 126 is attached to the front waist region 116 of the diaper 110. Other suitable embodiments of the strip 680 are described in detail in U.S. patent application Ser. No. 13/953,380 filed Jul. 29, 2013 to Stabelfeldt et al. and titled ABSORBENT ARTICLE HAVING A FASTENING SYSTEM, which is incorporated herein by reference in its entirety.

Figure 15:
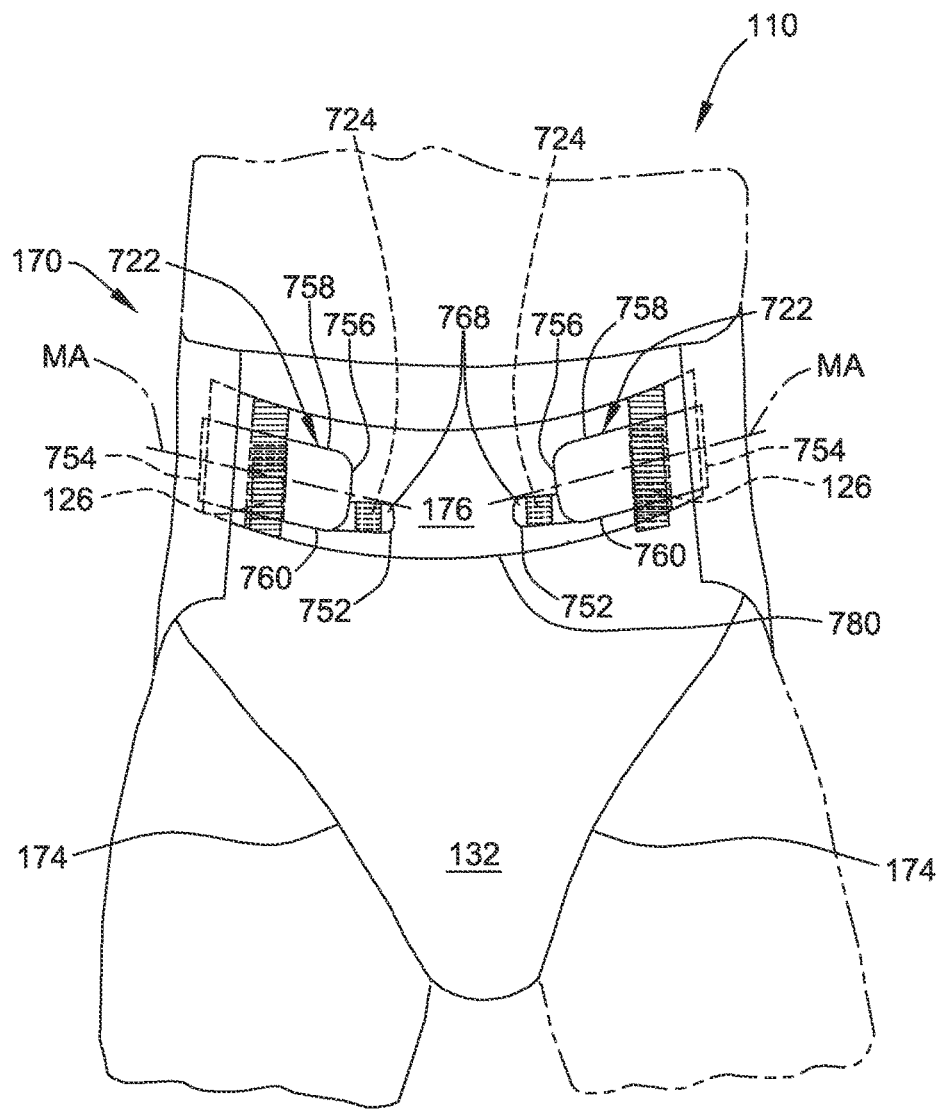
FIG. 15 is a front view of the diaper of FIG. 14 in a wear configuration and donned by a wearer with the fastening system fastened.

FIGS. 14 and 15 illustrate another suitable embodiment of the diaper 110 according to some aspects of the disclosure. The majority of the operable aspects of the diaper 110 seen in FIGS. 14 and 15 are the same or substantially similar to the embodiments depicted in the FIGS. 4-8. In this embodiment, however, the diaper 110 includes a pair of back ears, indicated generally at 722, having another suitable embodiment. Each of the back ears 722 includes an elastomeric portion 750, a non-elastomeric portion 752, and a primary first fastening component 724 mounted to the non-elastomeric portion (FIG. 14).

In this embodiment, each of the elastomeric portions 750 has a proximal edge 754, an opposed distal edge 756, an upper edge 758, and a lower edge 760. The proximal edge 754 of each of the elastomeric portions 750 is spaced inward from the respective side edge 128 of the diaper 110 such that a portion of the elastomeric portion overlaps the bodyside liner 130. The part of each of the elastomeric portions 750 overlapping the bodyside liner 130 is bonded (e.g., adhesive bonding, thermal bonding, both thermal and adhesive bonding) to at least the bodyside liner.

As seen in FIG. 14, the elastomeric portions 750 of each of the back ears 722 are angled relative to the longitudinal direction 112 of the diaper 110. More specifically, the upper and lower edges 758, 760 are angled downward (i.e., away from the back waist edge 138). Thus, the proximal edge 754 is disposed closer to the back waist edge 138 than the distal edge 756.

The elastomeric portions 750 of the back ears 722 can be formed from any type of elastomeric material capable of performing as described herein. In one suitable embodiment, the elastomeric material will be stretchable in at least one direction (e.g., in the lateral direction 114 of the diaper 110) and alternatively, the elastomeric material will be stretchable in two directions (e.g., in both the longitudinal direction 112 and the lateral direction of the diaper). Suitably when the elastomeric material is stretchable in a single direction, the stretch direction of the elastomeric material will be oriented so as to provide elastomeric forces which tend to pull the front and rear portions of the article towards one another such that the article is maintained about the waist of a wearer.

In one suitable embodiment, the elastomeric material from which the elastomeric portions 750 of the back ears 722 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 750 of the back ears 722 can be formed from a stretch-bonded-laminate (SBL) material, a neck-bonded-laminate (NBL) material, an elastomeric film, an elastomeric foam material, or the like.

Each of the non-elastomeric portions 752 of the back ears 722, which in this embodiment are tabs, is attached to a respective one of the elastomeric portions 750, and the primary first fastening components 724 (such as a hook material) are in turn disposed on the non-elastomeric portions. As illustrated in FIGS. 14 and 15, the non-elastomeric portions 752 of the back ears 722 extend in part transversely outward of the respective elastomeric portion 750 and the primary first fastening component 724 of each of the non-elastomeric portions are configured for engaging a loop component (e.g., the primary second fastening component 176) disposed in the front waist region 116 of the diaper 110 in the wear configuration.

With reference to FIG. 14, each of the elastomeric portions 750 of the back ears 722 have a medial line MA that divides the distal edge 756 of the elastomeric portion into an upper half and a lower half. In the illustrated embodiment and as seen in FIG. 14, the non-elastomeric portions 752 extend from the lower half (i.e., below the medial line MA) of each of the elastomeric portions 750 such that the entire non-elastomeric portion is disposed below the medial line. That is, no portion of the non-elastomeric portion 752 is disposed above the medial line MA of the elastomeric portion 750.

As seen best in FIG. 14, each of the illustrated non-elastomeric portions 752 further comprise a grip region 768 transversely outward of the primary first fastening component 724 for use in manually gripping and manipulating the non-elastomeric portion and more broadly the respective back ear 722 relative to the diaper 110. The grip region 768 is non-attachable to the diaper 110. In one embodiment, the grip region 768 extends transversely outward from the respective primary first fastening component 724 a distance of at least about 1 mm, such as in the range of about 1 mm to about 10 mm to provide sufficient unattached material for readily gripping and pulling on the non-elastomeric portion 752.

The diaper 110 can be selectively moved from the unfastened configuration, as illustrated in FIG. 14, to a fastened or wear configuration as illustrated in FIG. 15, by attaching the back ears 722 to the front waist region 116 using the article fastening system 170 to define a three-dimensional wear configuration of the diaper having a waist opening 172 and a pair of leg openings 174. The article fastening system 170 illustrated in FIGS. 14 and 15 comprises a primary fastening system and a secondary fastening system. The primary fastening system comprises the primary first fastening components 724 disposed on the non-elastomeric portions 752 of the back ears 722 and at least one corresponding primary second fastening component 176 which is adapted for refastenable engagement to the elastomeric portion 750.

In this embodiment, a strip 780, which is substantially similar to the strip 180 seen in FIGS. 6 and 7, comprising the primary second fastening component 176 and the secondary first fastening components 126 is attached to the front waist region 116 of the diaper 110. Other suitable embodiments of the strip 780 are described in detail in U.S. patent application Ser. No. 13/953,380 filed Jul. 29, 2013 to Stabelfeldt et al. and titled ABSORBENT ARTICLE HAVING A FASTENING SYSTEM, which is incorporated herein by reference in its entirety.

In one embodiment, the secondary first fastening components 126 (i.e., the hook fasteners of the illustrated embodiment) on the front portion 116 of the diaper 110 each have a relatively low stiffness at least in the longitudinal direction 112 of the diaper to facilitate decreased red marking of and discomfort to the wearer of the diaper. As used herein, the stiffness of the secondary first fastening components 126 refers generally to the resistance of each component to deflection or deformation (e.g., bending) when acted on by an applied force. For example, in one suitable embodiment, the stiffness may be a Gurley stiffness as determined in a Gurley Stiffness Test. In other embodiments the stiffness may be an edge stiffness as determined in an Edge Stiffness Test.

Gurley Stiffness Test

A Gurley Stiffness Test is commonly used to determine the stiffness of a test specimen (such as, e.g., the secondary first fastening component 126) with respect to a bending moment produced by a force that is directed perpendicular to the plane substantially defined by the length and width of the specimen being tested. A description of a Gurley Stiffness Test is set forth in TAPPI Standard Test T543 om-94 (Bending Resistance of Paper (Gurley type tester). One suitable testing apparatus for conducting the Gurley Stiffness Test is a Gurley Digital Stiffness Tester, Model 31644 manufactured by Teledyne Gurley, a business having offices in Troy, N.Y.

For purposes of the present disclosure, the stated Gurley stiffness values are those that would be generated by a standard sized sample (i.e., 1 inch wide by 3.5 inches long) using the Gurley Digital Stiffness Tester. Accordingly, the readings from the Tester are appropriately converted to the stiffness of a standard sized sample (i.e., 1 inch wide by 3.5 inches long), and are reported in terms of milligrams (mg) of force.

In general, the Gurley Digital Stiffness Tester consists of a pendulum with slots for attaching various weights. The specimen to be tested presses the pendulum to the right and to the left resulting in two readings. The readings are positively correlated with a specimen's stiffness. The two readings are then averaged and multiplied by a factor. This factor is determined by the specimen size, the distance from the center pivot, and the weight used on the pendulum. Methodology of the Gurley Stiffness Test is set forth below.

For purposes of the present disclosure, test specimens are prepared, e.g., taken from a larger sample or product, by cutting the specimen to have its length in the longitudinal or machine direction of the product. As an example, for the present disclosure where the secondary first fastening components (e.g., hook fasteners) are being tested, the specimens are cut from the diaper to include the fastener along with the material to which it is attached, e.g., the outer cover of the diaper. Each specimen should be cut to 12 mm wide by 25 mm long±1 mm (or 0.5 inches by 1 inch±0.04 inches).

To conduct the Gurley Stiffness Test using the Gurley Digital Stiffness Tester, the base of the instrument is first leveled by adjusting the leveling screw until the level's bubble is centered and the pendulum's pointer indicates zero. After turning the power on, the specimen is used to determine the appropriate weight and the weight position on the pendulum to obtain a reading between 2 and 6 on the scale/display. The switches are set to correspond to the weight being used, the weight's position on the pendulum, the width of the specimen being tested, and the length of the specimen.

For each specimen, the specimen strip is centered over the pendulum such that 6.4 mm±1 mm (or 0.25 inches±0.04 inches) overlaps the top of the pendulum and 6.4 mm±1 mm (or 0.25 inches±0.04 inches) is held in the jaws of the Tester. The system is reset so that the display reads 00-000-00. The Motor-Direction switch is operated to engage the clamp arm to press the specimen against the pendulum. Both a left reading and a right reading are taken, and an average reading is determined. The SELECT button on the Tester is then pressed to obtain the stiffness (in milligrams) calculation and the stiffness is recorded. The aforementioned steps are repeated for each test specimen in the sample group.

EXAMPLE

Secondary first fastening components from two different absorbent products were subjected to the Gurley Stiffness Test to assess the relative Gurley stiffness of each. The first product was the KC-Mexico diaper, which has fastening components being hook fasteners and being made of polypropylene. Each specimen had the following test conditions: weight 25 g, and weight position 4"; and measurements: width 0.5", and length 1". The second product was made in accordance with the present disclosure with the fastening components being hook fasteners and being made of polyethylene. Each specimen had the following test conditions: weight 25 g, and weight position 2"; and measurements: width 0.5", and length 1". Ten specimens of each product were tested. As used herein when referring to the Gurley Stiffness test, "length" generally refers to a direction in the longitudinal direction of the product, and "width" generally refers to a dimension in the lateral direction of the product. Further, "weight" and "weight position" generally refer to test conditions which indicate how much force is attached to the pendulum and at what position during the test.

Table 1 below is the results of the Gurley Stiffness Test for the KC-Mexico diaper and Table 2 is the results for the product according to the present disclosure.

TABLE 1

KC-Mexico Diaper Gurley Stiffness Test results

| Spec. | Right | Left | Ave. | Stiffness (mg) |
|---|---|---|---|---|
| 1 | 3.30 | 4.80 | 4.05 | 225.18 |
| 2 | 2.50 | 4.60 | 3.55 | 197.38 |
| 3 | 3.00 | 4.60 | 3.80 | 211.28 |
| 4 | 2.60 | 4.10 | 3.35 | 186.26 |
| 5 | 3.00 | 4.40 | 3.70 | 205.72 |
| 6 | 2.90 | 3.80 | 3.35 | 186.26 |
| 7 | 2.10 | 4.70 | 3.40 | 189.04 |
| 8 | 3.70 | 4.10 | 3.90 | 216.84 |
| 9 | 3.10 | 5.70 | 4.40 | 244.64 |
| 10 | 2.70 | 5.10 | 3.90 | 216.84 |
| Ave. | 2.89 | 4.59 | 3.74 | 207.94 |
| Std. | 0.45 | 0.55 | 0.34 | 18.94 |

TABLE 2

Present disclosure product Gurley Stiffness Test results

| Spec. | Right | Left | Ave. | Stiffness (mg) |
|---|---|---|---|---|
| 1 | 1.40 | 2.80 | 2.10 | 116.76 |
| 2 | 1.70 | 3.70 | 2.70 | 150.12 |
| 3 | 1.90 | 2.90 | 2.40 | 130.44 |
| 4 | 1.50 | 3.00 | 2.25 | 125.10 |
| 5 | 1.60 | 2.70 | 2.15 | 119.54 |
| 6 | 1.90 | 4.40 | 3.15 | 175.14 |
| 7 | 1.70 | 2.70 | 2.20 | 122.32 |
| 8 | 1.70 | 2.70 | 2.20 | 122.32 |
| 9 | 1.30 | 3.10 | 2.20 | 122.32 |
| 10 | 2.00 | 4.50 | 3.25 | 180.70 |
| Ave. | 1.67 | 3.25 | 2.46 | 136.48 |
| Std. | 0.23 | 0.70 | 0.43 | 23.76 |

The tested fastening components from the KC-Mexico diaper had an average stiffness of 207.94 mg whereas the tested fastening components from the present disclosure product had an average stiffness of 136.48 mg. Additionally, the tested fastening components from the KC-Mexico diaper ranged from a minimum stiffness of 186.26 mg to a maximum stiffness of 244.64 mg. The tested fastening components from the present disclosure product ranged from a minimum stiffness of 116.76 mg to a maximum stiffness of 180.70 mg. In other words, the minimum stiffness (186.26 mg) of the tested components of the KC-Mexico diaper was greater than the maximum stiffness (180.70 mg) of the tested fastening components from the present disclosure product. Put differently, every tested fastening component from the present disclosure product had a Gurley stiffness of less than 185 mg.

To this end, in one suitable embodiment of the present disclosure, the secondary first fastening component 126, and more particularly the secondary hook fastener on the front portion 116 of the diaper 110 as in the illustrated embodiment, has a Gurley stiffness according to the Gurley Stiffness Test of less than 185 mg, more suitably less than 170 mg, even more suitably less than 160 mg, still more suitably less than 150 mg, and still more suitably less than 140 mg. In another suitable embodiment, the secondary first fastening component 126, and more particularly the secondary hook fastener on the front portion 116 of the diaper 110 as in the illustrated embodiment, has an average Gurley stiffness according to the Gurley Stiffness Test of less than 180 mg for a sample size of at least 10 specimens, more suitably less than 170 mg, even more suitably less than 160 mg, still more suitably less than 150 mg, and still more suitably less than 140 mg. It is understood that in other embodiments the Gurley stiffness, and/or the average Gurley stiffness of the secondary first fastening component 126 may be even less than the ranges set forth above and remain within the scope of the disclosure.

Edge Stiffness Test

An Edge Stiffness Test determines the edge stiffness of a test specimen 500 (such as, e.g., the secondary first fastening component 126), and more particularly it measures the amount of force, in grams (grams-force, or gf), required to buckle or bend upon applying a longitudinal force against an edge of the specimen. This is indicative, for example, of the manner in which a force would be applied by a wearer to the secondary first fastening components 126 of the diaper 110 when the wearer bends over at the waist.

Figure 16:
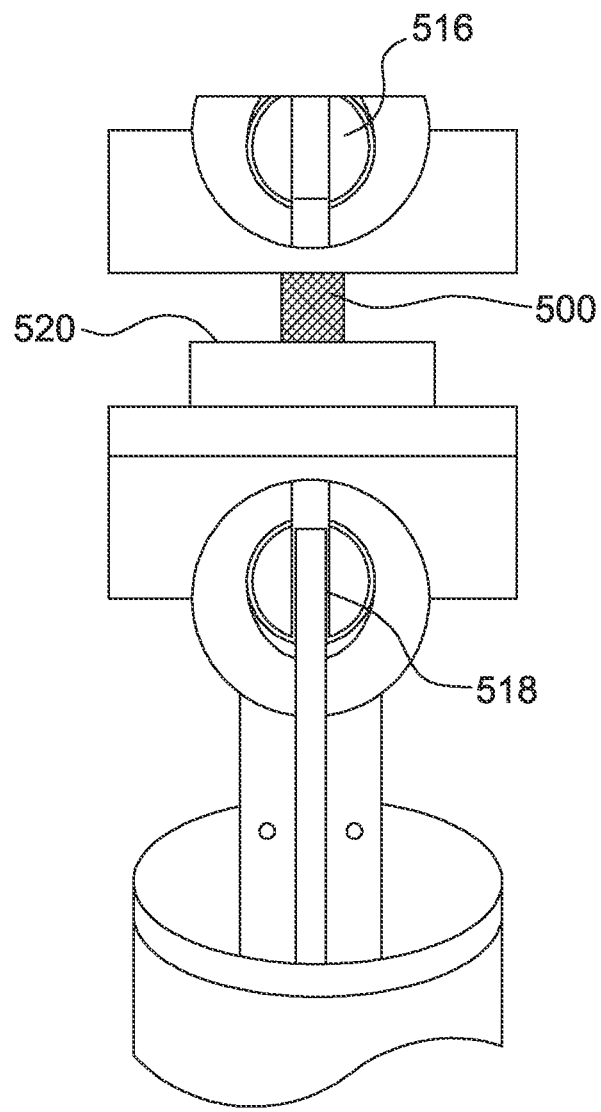
FIG. 16 is a perspective of a test specimen provided in a testing machine according to the Edge Stiffness Test.

Turning now to FIG. 16, a rectangular (elongate) specimen 500 is held upright (i.e., lengthwise) by a grip, or jaws (i.e., upper jaw 516 and lower jaw 518), with the short edge or end of the specimen perpendicular to and in contact with a flat surface or platen 520. The contact edge is then gradually urged against the flat surface by moving the grip or jaws 516, 518 toward the flat surface 520 by a recorded distance until the specimen buckles or bends. As can be seen from FIG. 17, which is a plot of compression force versus compression distance (i.e., the distance that the grip or jaws 516, 518 move toward the flat surface during testing) and is described in further detail later herein, the compression force initially increases proportionately with compressed distance, i.e., the distance that the grip or jaws move toward the flat surface 520. After reaching a peak compression force, the force decreases asymptotically toward a constant while the compressed distance increases. The edge stiffness is the peak compression force achieved during the test, with a lower compression force meaning that the specimen 500 has a lower edge stiffness, or is more easily bent upon application of a force to the edge of the specimen.

One suitable testing apparatus for conducting the Edge Stiffness Test is an MTS Sintech tensile frame 500S manufactured by MTS System Corporation, a business having offices in Eden Prairie, Minn. Additional instruments used to conduct the Edge Stiffness Test include a load cell 100 Newton D86201, an upper fixture having a upper jaw 516 measuring 1" long and 3" wide, and a low fixture stainless steel platen 520 having a diameter measuring 3.5" (all manufactured by MTS System Corporation). Also used is a thickness measurement device such as a Sony Digital Indicator U30A equipped with a 0.05 psi platen, manufactured by Sony Corporation of America, a business having offices in New York, N.Y.

To conduct the Edge Stiffness Test for the purposes of the present disclosure, specimens 500 are cut to have a width of 15 mm in the lateral direction 114 of the product, such as the diaper 110 of the illustrated embodiment, and a length of 40 mm in the longitudinal direction 112 of the product. The thickness of each specimen 500 is measured using the thickness measurement device with a 0.05 psi platen to the nearest 0.001 mm. The distance between the lower platen 520 and the bottom of the upper jaw 516 is set at 10 mm and the specimen 500 is placed in the upper jaw with the specimen oriented lengthwise. The lower edge of the specimen 500 is in slight contact with the flat surface of the lower platen 520.

The upper jaw 516 is activated to move downward toward the lower platen 520 at a speed of 6.35 mm/min. (0.25 inches/min.) to longitudinally compress the specimen 500 until the force drops from the peak and levels off. Test data of the compression force vs. compression distance (e.g., downward travel distance of the upper jaw 516) is recorded on a PC using software having the trade name TestWorks V4.12C provided by MTS System Corporation. The compression force is reported to the nearest 0.1 grams-force (gf). The peak compression load (in gf) for each specimen 500 tested is determined using this software. The peak compression stress in $gf/mm^2$ is calculated by dividing the peak compression load in gf by the cross sectional area in $mm^2$.

EXAMPLE

Secondary first fastening components from two different absorbent products were subjected to the Edge Stiffness Test to assess the relative edge stiffness of each. The first product was the KC-Mexico diaper having hook fasteners made of polypropylene. The second product was a diaper 110 made in accordance with the present disclosure with the secondary first fastening components 126 being hook fasteners and being made of polyethylene. Five specimens 500 of each product were tested.

Table 3 below is the results of the Edge Stiffness Test for the KC-Mexico diaper and Table 4 is the results for the product according to the present disclosure. The Peak Load is the edge stiffness, in grams-force (gf).

TABLE 3

KC-Mexico Diaper Edge Stiffness Test results

| Spec. | Thickness (mm) | Width (mm) | Peak Load (gf) | Peak Stress ($gf/mm^2$) |
| --- | --- | --- | --- | --- |
| 1 | 0.728 | 15 | 115 | 10.5 |
| 2 | 0.72 | 15 | 158.2 | 14.6 |
| 3 | 0.761 | 15 | 100.1 | 8.8 |
| 4 | 0.768 | 15 | 149.5 | 13.0 |
| 5 | 0.689 | 15 | 110.7 | 10.7 |
| Ave | 0.733 | 15 | 126.7 | 11.5 |
| Std | 0.032 | 0 | 25.6 | 2.3 |

TABLE 4

Present disclosure product Edge Stiffness Test results

| Spec. | Thickness (mm) | Width (mm) | Peak Load (gf) | Peak Stress ($gf/mm^2$) |
| --- | --- | --- | --- | --- |
| 1 | 0.651 | 15 | 68.2 | 7.0 |
| 2 | 0.772 | 15 | 38.5 | 3.3 |
| 3 | 0.735 | 15 | 43.7 | 4.0 |
| 4 | 0.768 | 15 | 53.4 | 4.6 |
| 5 | 0.739 | 15 | 40.6 | 3.7 |
| Ave | 0.733 | 15 | 48.9 | 4.5 |
| Std | 0.049 | 0 | 12.2 | 1.5 |

Figure 17:
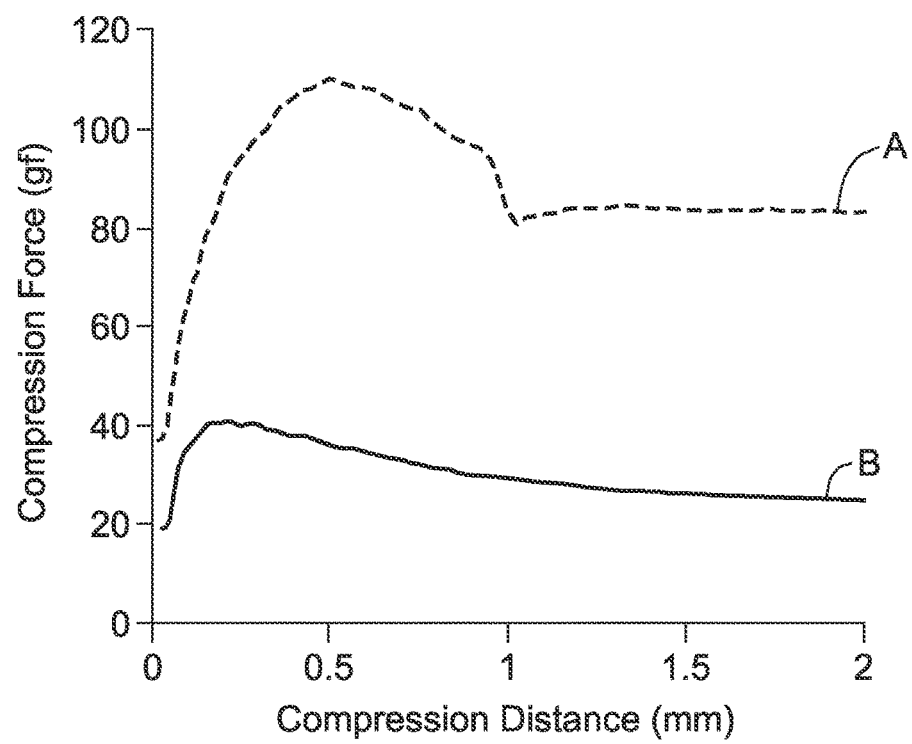
FIG. 17 is a plot of compression force vs. compression distance for a specimen of a prior art product and a specimen of one embodiment of the present disclosure product according to an Edge Stiffness Test as described herein.

FIG. 17 is a plot of compression force vs. compression distance for specimen #5 of the KC-Mexico diaper (trend line A) and specimen #5 of the present disclosure product (trend line B) of the above Edge Stiffness Test. Each curve shows the amount of force needed to bend or buckle the specimen upon applying a force to the edge of the specimen. For instance, trend line B indicates that the compression force required to bend or buckle the specimen from a product made in accordance with the present disclosure increased until the specimen buckled at a peak compression force of 40.6 grams-force (after only a slight amount of compression distance). After the peak compression load, the compression force required to further bend the specimen 500 decreased asymptotically towards approximately 20 grams-force.

Trend line A indicates that the compression force required to bend or buckle the specimen 500 from the KC-Mexico diaper increases until the specimen buckled at a peak compression force of 110.7 grams-force. After the peak compression load, the compression force required to further bend the specimen 500 decreased asymptotically towards approximately 80 grams-force. Accordingly, it required more force to compress the edge of a specimen 500 from the KC-Mexico diaper than it did to compress the edge of a specimen from a product made according to present disclosure. Therefore, it can be concluded that the edge stiffness of the secondary first fastening component 126 of the present disclosure product was less stiff than that of the KC-Mexico diaper.

Accordingly, in one embodiment the secondary first fastening component 126, and more particularly the secondary hook fastener on the front portion 116 of the diaper 110 as in the illustrated embodiment, has an edge stiffness according to the Edge Stiffness Test of less than 100 grams-force, more suitably less than 90 grams-force, even more suitably less than 80 grams-force, still more suitably less than 70 grams-force, and still more suitably less than 60 grams-force. In other embodiments it is less than 50 grams-force.

In another embodiment the secondary first fastening component 126, and more particularly the secondary hook fastener on the front portion 116 of the diaper 110 as in the illustrated embodiment, has an average edge stiffness according to the Edge Stiffness Test of less than 80 grams-force for a sample size of at least 5 specimens, more suitably less than 70 grams-force, even more suitably less than 60 grams-force, and still more suitably less than 50 grams-force. It is understood that in other embodiments the edge stiffness and/or the average edge stiffness of the secondary first fastening component 126 may be even less than the ranges set forth above and remain within the scope of the disclosure.

With reference to Tables 3 and 4, the KC-Mexico diaper specimens 500 had an average peak load of 126.7 grams-force whereas the present disclosure specimens had an average peak load of 48.9 grams-force. Another embodiment of the present disclosure has an average peak load of less than 90 grams-force based on a sample size of at least 5 samples. Another embodiment of the present disclosure with a sample size of at least 5 samples has an average peak load of less than 80 grams-force. Yet another embodiment of the present disclosure with a sample size of at least 5 samples has an average peak load of less than 70 grams-force. Yet another embodiment of the present disclosure with a sample size of at least 5 samples has an average peak load of less than 60 grams-force.

With continued reference to Tables 3 and 5, the KC-Mexico diaper specimens 500 shown in Table 3 ranged from a minimum peak load of 100.1 grams-force to a maximum peak load of 158.2 grams-force. The present disclosure specimens 500 shown in Table 4 ranged from a minimum peak load of 38.5 grams-force to a maximum peak load of 68.2 grams-force. In other words, every specimen 500 in the present disclosure sample had a peak load of less than 100 grams-force.

Thus, in view of either one of the Gurley Stiffness Test and the Edge Stiffness Test, particularly as used in the above Examples, it is evident that the secondary first fastening components 126 are less stiff than secondary first fastening components of the KC-Mexico diaper. As used on the diaper 110 described herein, such a reduced stiffness increases comfort for the wearer and reduces red marks that may irritate the skin.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article having an inner surface, an outer surface, a first waist portion, a second waist portion, a crotch portion extending longitudinally between and connecting the first waist portion and the second waist portion, the absorbent article comprising:
   a chassis having longitudinally opposite ends, transversely opposite sides, a bodyside liner at least in part defining the inner surface of the article, an outer cover at least in part defining the outer surface of the article, and an absorbent core disposed between the liner and the outer cover;
   a pair of ears extending transversely outward from the opposite sides of the chassis at the second waist portion thereof; and
   a fastening system comprising a primary fastening system and a secondary fastening system, the primary fastening system comprising a primary first fastening component located on each of the pair of ears and a primary second fastening component, the secondary fastening system comprising a secondary second fastening component located on each of the ears and corresponding secondary first fastening components, a non-linear strip attached to the outer surface of the article at the first waist portion, the primary second fastening component and the secondary first fastening components being located on the non-linear strip, wherein the strip is arcuate, the strip comprising an arcuate upper edge, an arcuate lower edge and a pair of side edges extending between the upper and lower edges.

2. The absorbent article set forth in claim 1 wherein at least the upper edge of the strip has a radius between 155 mm and 1,740 mm.

3. The absorbent article set forth in claim 1 wherein the strip is defined by the primary second fastening component.

4. An absorbent article having an inner surface, an outer surface, a first waist portion, a second waist portion, a crotch portion extending longitudinally between and connecting the first waist portion and the second waist portion, the absorbent article comprising:
   a chassis having longitudinally opposite ends, transversely opposite sides, a bodyside liner at least in part defining the inner surface of the article, an outer cover at least in part defining the outer surface of the article, and an absorbent core disposed between the liner and the outer cover;
   a pair of ears extending transversely outward from the opposite sides of the chassis at the second waist portion thereof; and
   a fastening system comprising a primary fastening system and a secondary fastening system, the primary fastening system comprising a primary first fastening component located on each of the pair of ears and a primary second fastening component, the secondary fastening system comprising a secondary second fastening component located on each of the ears and corresponding secondary first fastening components, a non-linear strip attached to the outer surface of the article at the first waist portion, the primary second fastening component and the secondary first fastening components being located on the non-linear strip, wherein the strip comprises a straight central portion and a pair of angled portions with each of the angled portions flanking opposite sides of the straight portion, the straight central portion comprising the primary second fastening component, and the angled portions comprising the secondary first fastening components.

5. The absorbent article set forth in claim 4 wherein each of the angled portions of the strip angle upward and outward from a respective side of the straight central portion towards the first waist edge and the respective side edge.

6. The absorbent article set forth in claim 4 wherein the angled portions are formed separately from the straight central portion.

7. An absorbent article having an inner surface, an outer surface, a first waist portion, a second waist portion, a crotch portion extending longitudinally between and connecting the first waist portion and the second waist portion, the absorbent article comprising:
   a chassis having longitudinally opposite ends, transversely opposite sides, a bodyside liner at least in part defining the inner surface of the article, an outer cover at least in part defining the outer surface of the article, and an absorbent core disposed between the liner and the outer cover;
   a pair of ears extending transversely outward from the opposite sides of the chassis at the second waist portion thereof; and
   a fastening system comprising a primary fastening system and a secondary fastening system, the primary fastening system comprising a primary first fastening component located on each of the pair of ears and a primary second fastening component, the secondary fastening system comprising a secondary second fastening component located on each of the ears and corresponding secondary first fastening components, a non-linear strip attached to the outer surface of the article at the first waist portion, the primary second fastening component and the secondary first fastening components being located on the non-linear strip, the non-linear strip having a pair of spaced cutouts, each of the cutouts including one of the secondary first fastening components.

8. The absorbent article set forth in claim 7 wherein each of cutouts is arcuate.

9. The absorbent article set forth in claim 8 wherein each of the arcuate cutouts has approximately the same radius as an adjacent portion of the side edges.

10. The absorbent article set forth in claim 7 wherein the strip comprises an upper edge, a lower edge and a pair of side edges, each of the cutouts being disposed between the lower edge and one of the side edges.

11. An absorbent article having an inner surface, an outer surface, a first waist portion, a second waist portion, a crotch portion extending longitudinally between and connecting the first waist portion and the second waist portion, the absorbent article comprising:
- a chassis having longitudinally opposite ends, transversely opposite sides, a bodyside liner at least in part defining the inner surface of the article, an outer cover at least in part defining the outer surface of the article, and an absorbent core disposed between the liner and the outer cover;
- a pair of ears extending transversely outward from the opposite sides of the chassis at the second waist portion thereof, each of the ears having a medial line; and
- a fastening system comprising a primary fastening system and a secondary fastening system, the primary fastening system comprising a primary first fastening component located on each of the pair of ears and a primary second fastening component, the secondary fastening system comprising a secondary second fastening component located on each of the ears and corresponding secondary first fastening components, a non-linear strip attached to the outer surface of the article at the first waist portion, the primary second fastening component and the secondary first fastening components being located on the non-linear strip, each of the primary first fastening component being located below the medial line.

12. The absorbent article set forth in claim 11 wherein each ears includes an upper edge, a lower edge, a proximal edge, and a distal edge, the medial line being taken along the distal edge.

13. The absorbent article set forth in claim 11 wherein the medial line divides the respective ears into an upper half and a lower half, the primary first fastening components being located on the lower half.

14. The absorbent article set forth in claim 11 wherein the strip is arcuate.

15. The absorbent article set forth in claim 11 wherein each of the back ears includes an elastomeric portion and a non-elastomeric portion, the primary first fastening components being mounted to the respective non-elastomeric portion.

16. The absorbent article set forth in claim 15 wherein each of the non-elastomeric portions of the back ears is a tab.

17. The absorbent article set forth in claim 11 wherein at least a portion of each of the ears is elastomeric.

* * * * *